United States Patent
Al-Asad

(10) Patent No.: US 11,779,313 B2
(45) Date of Patent: Oct. 10, 2023

(54) SUPPRESSING SPECKLE NOISE IN MEDICAL ULTRASOUND IMAGES

(71) Applicant: Prince Mohammad Bin Fahd University, Dhahran (SA)

(72) Inventor: Jawad F. Al-Asad, Dhahran (SA)

(73) Assignee: Prince Mohammad Bin Fahd University, Dhahran (SA)

( * ) Notice: Subject to any disclaimer, the term of this patent is extended or adjusted under 35 U.S.C. 154(b) by 0 days.

(21) Appl. No.: 17/510,937

(22) Filed: Oct. 26, 2021

(65) Prior Publication Data

US 2023/0125188 A1    Apr. 27, 2023

(51) Int. Cl.
*A61B 8/08* (2006.01)
*G06T 7/00* (2017.01)

(52) U.S. Cl.
CPC .......... *A61B 8/5269* (2013.01); *A61B 8/5207* (2013.01); *A61B 8/5223* (2013.01); *A61B 8/5253* (2013.01); *G06T 7/0012* (2013.01); *G06T 2207/10132* (2013.01); *G06T 2207/30056* (2013.01); *G06T 2207/30084* (2013.01)

(58) Field of Classification Search
CPC .............................. G06T 7/0012; A61B 8/5269
See application file for complete search history.

(56) References Cited

U.S. PATENT DOCUMENTS 8,708,914 B2    4/2014   Suri
2006/0241410 A1 * 10/2006   Fang ................. A61B 5/05
                                               600/430

(Continued)

OTHER PUBLICATIONS

J. Baglama et al, "IRBL: An Implicitly Restarted Block-Lanczos Method for LargeScale Hermitian Eigenproblems", SIAM Journal on Scientific Computing, vol. 24, No. 5, pp. 1650-1677, 2003 (Year: 2003).*

(Continued)

*Primary Examiner* — Joel Lamprecht
*Assistant Examiner* — Nyrobi Celestine
(74) *Attorney, Agent, or Firm* — Oblon, McClelland, Maier & Neustadt, L.L.P.

(57) ABSTRACT

A method to suppresses speckle noise in medical ultrasound images includes ultrasound envelope image matrix A formed from the medical ultrasound images and segmented into overlapping segments, to form a sub-matrix B for each overlapping segment. A Hermitian covariance matrix C is formulated from column vectors Z. A global covariance matrix G is formed by averaging the C. A Lanczos decomposition is applied to the G to generate an orthonormal vector matrix composed of orthonormal vectors. A tridiagonal matrix H is generated. The orthonormal vectors are sorted based on magnitude of each column. An orthogonal projection matrix $P_{orth}$ is formed based on the orthonormal vectors. An estimated vector signal $\hat{Z}$ is obtained by projecting Z by $P_{orth}$. An estimated despeckled segment is formed from the $\hat{Z}$. An estimated despeckled ultrasound image is reconstructed by averaging each pixel by the number of segment updates.

11 Claims, 21 Drawing Sheets

(56) References Cited

U.S. PATENT DOCUMENTS

2010/0239103 A1* 9/2010 Barbotin ............... H04B 1/719
  381/94.1
2013/0188854 A1* 7/2013 Bilgic ................... A61B 5/055
  382/131
2019/0295295 A1* 9/2019 Hyun ................... A61B 8/5207

OTHER PUBLICATIONS

S. Aliabadi et al, "Eigenspace based beamformer using oblique signal subspace projection for ultrasound plane wave imaging", BioMedical Engineering OnLine, vol. 15, No. 127, pp. 1-19, 2016 (Year: 2016).*

M. Butt et al, "Ultrasound Image Denoising Using Orthogonal Decomposition in Frequency Domain", 2019 IEEE 9th International Conference on System Engineering and Technology (ICSET), p. 1-6, Oct. 2019 (Year: 2019).*

Jawad F. Al-Asad, et al., "QR based De-noising Scheme for Medical Ultrasound Images", $9^{th}$ IEEE-GCC Conference and Exhibition (GCCCE), May 8-11, 2017, 4 pages.

Muhammad O. Butt, et al., "Ultrasound Image Denoising Using Orthogonal Decomposition in Frequency Domain", IEEE $9^{th}$ International Conference on System Engineering and Technology (ICSET), Oct. 7, 2019, pp. 349-353.

\* cited by examiner

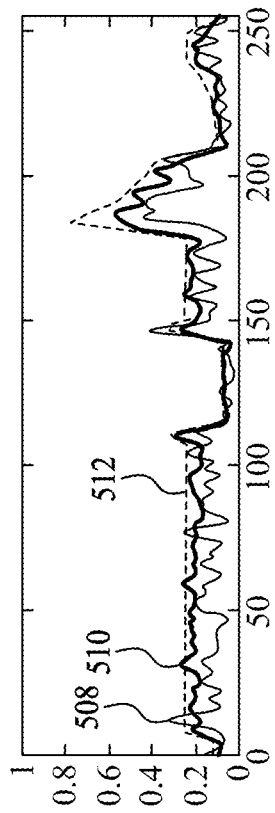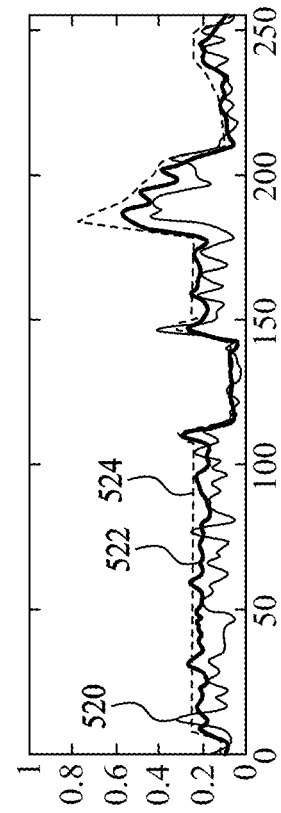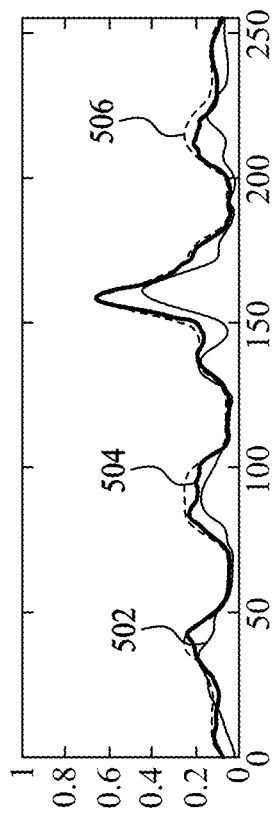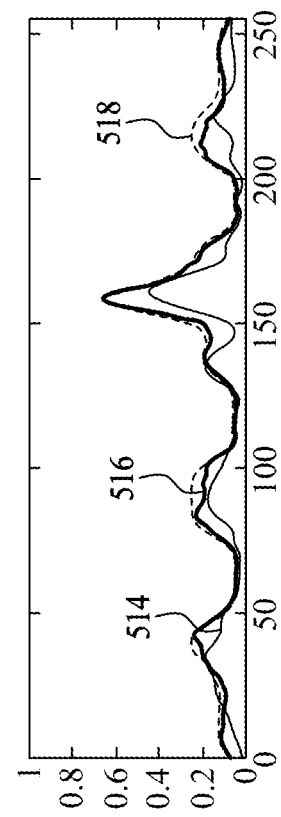

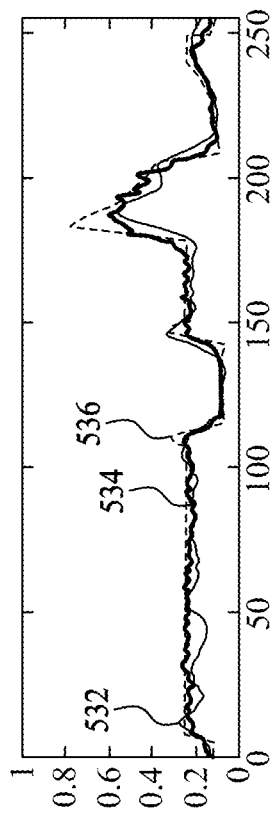
FIG. 5C(1)
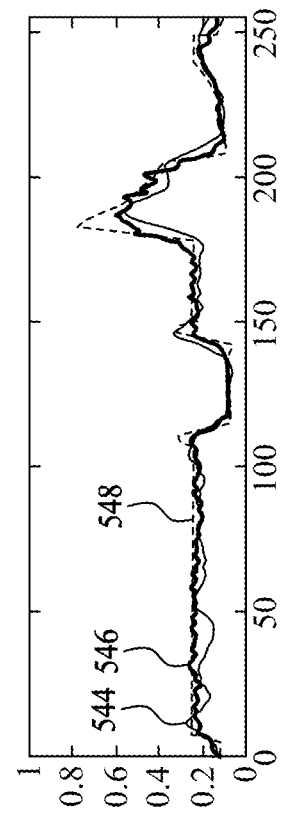
FIG. 5C(2)
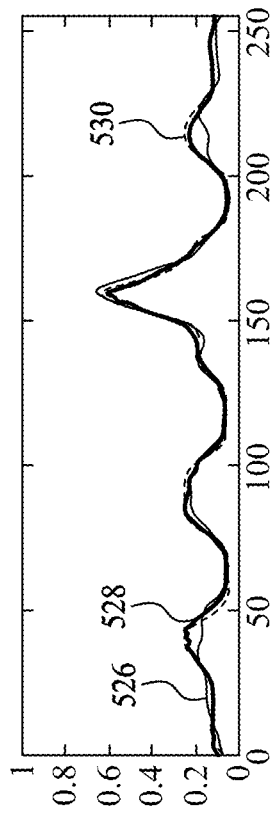
FIG. 5D(1)
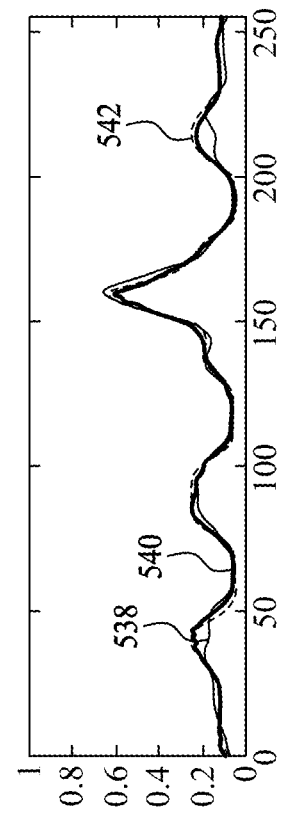
FIG. 5D(2)

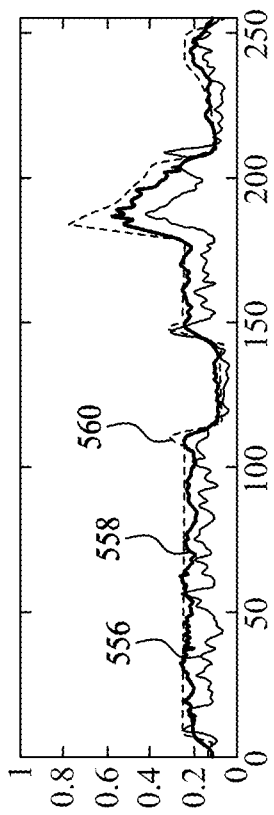
FIG. 5E(1)
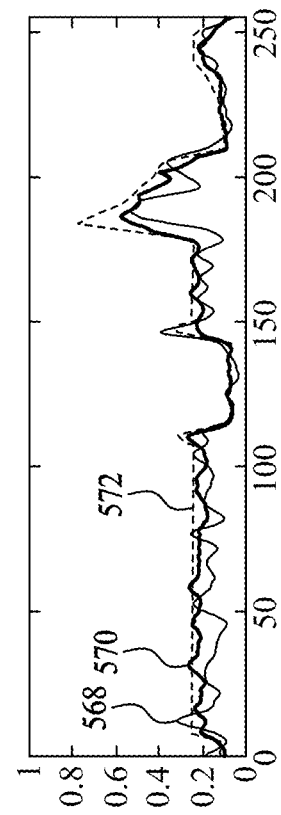
FIG. 5E(2)
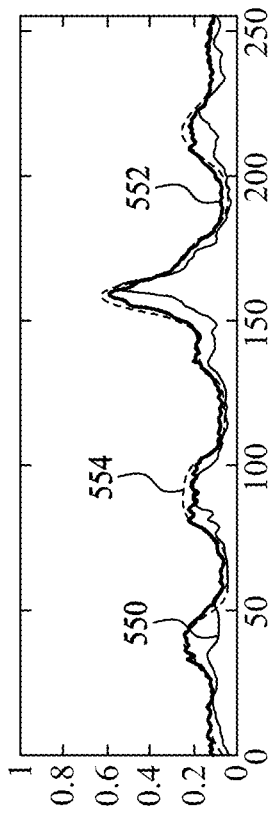
FIG. 5F(1)
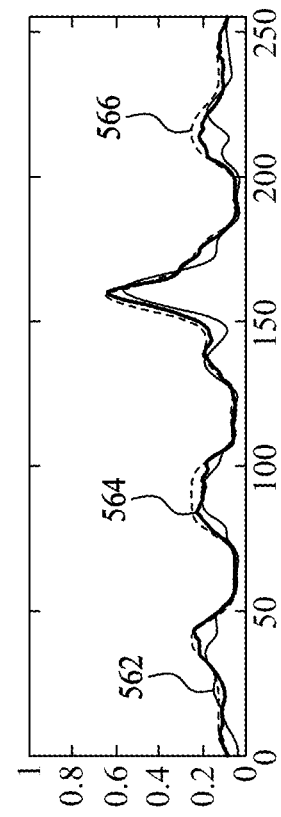
FIG. 5F(2)

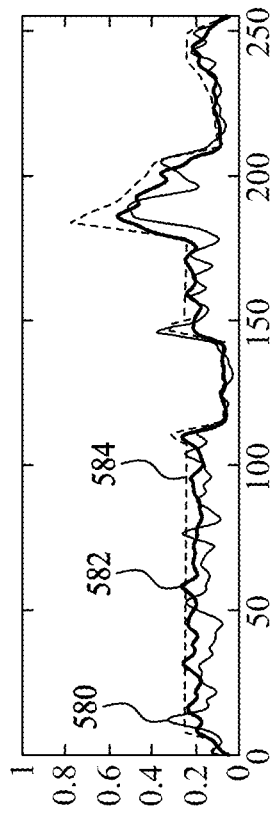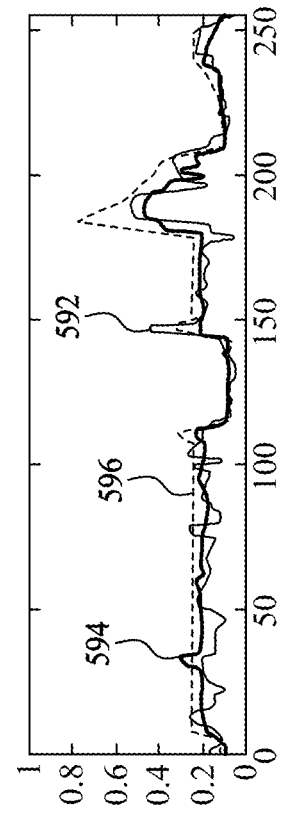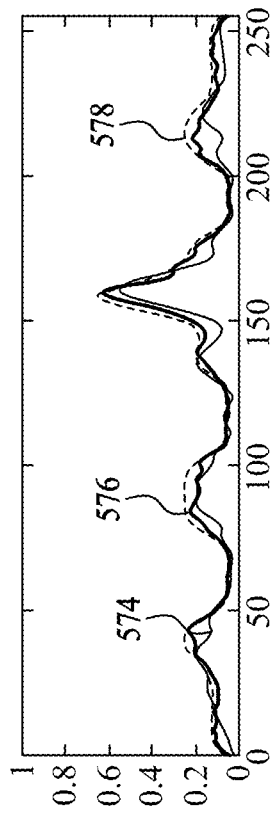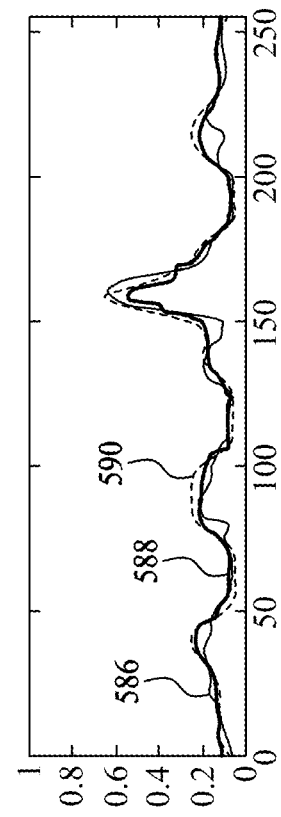
FIG. 5G(1)  FIG. 5G(2)  FIG. 5H(1)  FIG. 5H(2)

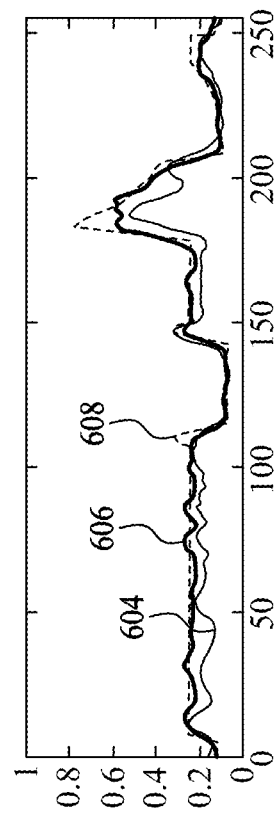
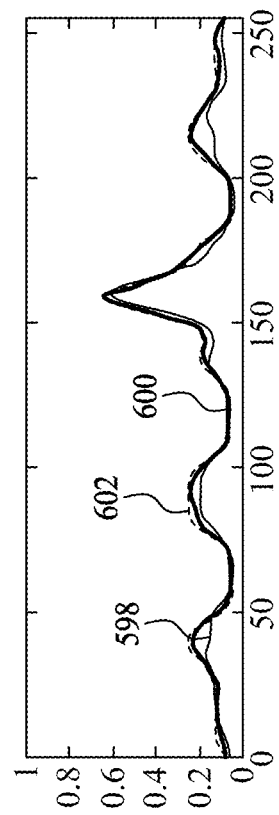
FIG. 5I(2)
FIG. 5I(1)

SUPPRESSING SPECKLE NOISE IN MEDICAL ULTRASOUND IMAGES

BACKGROUND

Technical Field

The present disclosure is directed to methods for suppressing speckle noise in medical ultrasound images.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Ultrasound imaging is a widely used imaging modality for medical diagnosis because of its high efficacy, low cost, and real-time noninvasive imaging nature. Ultrasound imaging uses sound waves exceeding 20 kHz frequency to generate imagery of internal body organs, without the health risks associated with radiation imaging. The reflected sound waves from the internal body organs are captured for processing. However, the quality of an ultrasound image is degraded due to multipath echoes from internal body parts, causing noise. This noise is usually referred to as speckle noise and is multiplicative in nature. The speckle noise is random and granular in appearance. The speckle noise degrades the contrast of image significantly and may obstruct details of interest.

Numerous studies relating to hardware design as well as image processing have been conducted for ultrasound image quality enhancement. However, the current methods are insufficient in removing speckle noise. Accordingly, it is one object of the present disclosure to provide methods and systems for suppressing speckle noise in medical ultrasound images.

SUMMARY

In an exemplary embodiment, a method for suppressing speckle noise in medical ultrasound images is disclosed. The method includes receiving, by a computing device having circuitry and program instructions configured to be executed by one or more processors, an n×m ultrasound envelope image matrix A formed by a plurality of pixels of the medical ultrasound image, segmenting, by the computing device, an n×m ultrasound envelope image matrix A into a number of overlapping segments of r×p size, to form a sub-matrix B for each overlapping segment, where n is an axial image index, m is a lateral image index, $0 \leq r \leq n$ and $0 \leq p \leq m$, reshaping each sub-matrix B into a column vector Z of size r·p×1, formulating a Hermitian covariance matrix C from the column vectors Z, forming a global covariance matrix G by averaging the Hermitian covariance matrices C by the number of overlapping segments of the image matrix A, applying Lanczos decomposition to the global covariance matrix G, generating an orthonormal vector matrix V composed of orthonormal vectors, v, generating a tridiagonal matrix H, summing each column of the tridiagonal matrix H to obtain a magnitude of each column, sorting the orthonormal vectors, v, of orthonormal vector matrix V in descending order based on the magnitude of each column, wherein sorting the orthonormal vectors divides the orthonormal vector matrix V into a signal subspace $V_1$ and a noise subspace $V_2$, forming an orthogonal projection matrix $P_{orth}$ from a first subset of the orthonormal vectors of signal subspace $V_1$, for each sub-matrix B, obtaining an estimated vector signal $\hat{Z}$ of size r·p×1 by projecting Z by $P_{orth}$, forming an estimated despeckled segment D of size r×p from the estimated vector signal $\hat{Z}$, reconstructing an estimated despeckled ultrasound image $\hat{I}$ by averaging each pixel of the plurality of pixels by the number of segment updates, and rendering, on a display of the computing device, the estimated despeckled ultrasound image $\hat{I}$.

In another exemplary embodiment, a method for suppressing speckle noise in medical ultrasound images is disclosed. The method includes receiving, by a computing device having circuitry and program instructions configured to be executed by one or more processors, an n×m ultrasound envelope image matrix A formed by a plurality of pixels of the medical ultrasound image, segmenting, by the computing device, an n×m ultrasound envelope image matrix A into a number of overlapping segments of r×p size, to form a sub-matrix B for each overlapping segment, where $0 \leq r \leq n$ and $0 \leq p \leq m$, reshaping each sub-matrix B into a column vector Z of size r·p×1, formulating a Hermitian covariance matrix C from the column vectors Z, forming a global covariance matrix G by averaging the Hermitian covariance matrices C by the number of overlapping segments of the image matrix A, applying Lanczos decomposition to the global covariance matrix G, generating an orthonormal vector matrix V composed of orthonormal vectors, v, generating a tridiagonal matrix H, summing each column of the tridiagonal matrix H to obtain a magnitude of each column, sorting the orthonormal vectors of orthonormal vector matrix V in descending order based on the magnitude of each column, wherein sorting the orthonormal vectors divides the orthonormal vector matrix V into a signal subspace $V_1$ and a noise subspace $V_2$, forming an orthogonal projection matrix $P_{orth}$ from a first subset of the orthonormal vectors of signal subspace $V_1$, forming an oblique projection matrix $P_{obli}$ from the orthonormal vectors V by subtracting each noise subspace $V_2$ from orthonormal vector matrix V, for each sub-matrix B, obtaining an estimated vector signal $\hat{Z}'$ of size r·p×1 by projecting Z by $P_{obli}$, forming an estimated despeckled segment D of size r×p from the estimated vector signal $\hat{Z}'$, reconstructing an estimated despeckled ultrasound image $\hat{I}$ by averaging each pixel of the plurality of pixels by the number of segment updates, and rendering, on a display of the computing device, the estimated despeckled ultrasound image $\hat{I}$.

In another exemplary embodiment, a non-transitory computer readable medium having instructions stored therein that, when executed by one or more processors, cause the one or more processors to perform a method for suppressing speckle noise in medical ultrasound images. The method includes receiving, by a computing device having circuitry and program instructions configured to be executed by one or more processors, an n×m ultrasound envelope image matrix A formed by a plurality of pixels of the medical ultrasound image, segmenting, by the computing device, an n×m ultrasound envelope image matrix A into a number of overlapping segments of r×p size, to form a sub-matrix B for each overlapping segment, where n is an axial image index, m is a lateral image index, $0 \leq r \leq n$ and $0 \leq p \leq m$, reshaping each sub-matrix B into a column vector Z of size r·p×1, formulating a Hermitian covariance matrix C from the column vectors Z, forming a global covariance matrix G by averaging the Hermitian covariance matrices C by the number of overlapping segments of the image matrix A, applying Lanczos decomposition to the global covariance matrix G, generating an orthonormal vector matrix V composed of orthonormal vectors, v, generating a tridiagonal matrix H, summing each column of the tridiagonal matrix H to obtain a magnitude of each column, sorting the orthonormal vectors, v, of orthonormal vector matrix V in descending order based on the magnitude of each column, wherein sorting the orthonormal vectors divides the orthonormal vector matrix V into a signal subspace $V_1$ and a noise subspace $V_2$, and forming an orthogonal projection matrix $P_{orth}$ from a first subset of the orthonormal vectors of signal subspace $V_1$.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 5A(1) illustrates a lateral profile corresponding to a singular value decomposition (SVD) orthogonal subspace projection associated with a corresponding image in FIG. 2B and FIG. 2C, according to certain embodiments FIG. 5A(2) illustrates an axial profile corresponding to the SVD orthogonal subspace projection associated with a corresponding image in FIG. 2B and FIG. 2C, according to certain embodiments.

FIG. 5B(1) illustrates a lateral profile corresponding to the SVD orthogonal subspace projection associated with a corresponding image in FIG. 2B and FIG. 2C, according to certain embodiments.

FIG. 5B(2) illustrates an axial profile corresponding to the SVD oblique subspace projection associated with a corresponding image in FIG. 2B and FIG. 2C, according to certain embodiments.

FIG. 5C(1) illustrates a lateral profile corresponding to a Lanczos orthogonal subspace projection associated with a corresponding image in FIG. 2B and FIG. 2C, according to certain embodiments.

FIG. 5C(2) illustrates an axial profile corresponding to the Lanczos orthogonal subspace projection associated with a corresponding image in FIG. 2B and FIG. 2C, according to certain embodiments.

FIG. 5D(1) illustrates a lateral profile corresponding to a Lanczos oblique subspace projection associated with a corresponding image in FIG. 2B and FIG. 2C, according to certain embodiments.

FIG. 5D(2) illustrates an axial profile corresponding to the Lanczos oblique subspace projection associated with a corresponding image in FIG. 2B and FIG. 2C, according to certain embodiments. FIG. 5E(1) illustrates a lateral profile corresponding to a probabilistic non local means (PNLM) subspace projection associated with a corresponding image in FIG. 2B and FIG. 2C, according to certain embodiments.

FIG. 5E(2) illustrates an axial profile corresponding to the PNLM subspace projection associated with a corresponding image in FIG. 2B and FIG. 2C, according to certain embodiments.

FIG. 5F(1) illustrates a lateral profile corresponding to a Frost subspace projection associated with a corresponding image in FIG. 2B and FIG. 2C, according to certain embodiments.

FIG. 5F(2) illustrates an axial profile corresponding to the Frost subspace projection associated with a corresponding image in FIG. 2B and FIG. 2C, according to certain embodiments.

FIG. 5G(1) illustrates a lateral profile corresponding to a Lee subspace projection associated with a corresponding image in FIG. 2B and FIG. 2C, according to certain embodiments.

FIG. 5G(2) illustrates an axial profile corresponding to the Lee subspace projection associated with a corresponding image in FIG. 2B and FIG. 2C, according to certain embodiments.

FIG. 5H(1) illustrates a lateral profile corresponding to a geometric nonlinear diffusion filter (GNLDF) subspace projection associated with a corresponding image in FIG. 2B and FIG. 2C, according to certain embodiments.

FIG. 5H(2) illustrates an axial profile corresponding to the GNLDF subspace projection associated with a corresponding image in FIG. 2B and FIG. 2C, according to certain embodiments FIG. 5I(1) illustrates a lateral profile corresponding to a guided speckle reducing bilateral filter (GSRBF) subspace projection associated with a corresponding image in FIG. 2B and FIG. 2C, according to certain embodiments.

FIG. 5I(2) illustrates an axial profile corresponding to the GSRBF subspace projection associated with a corresponding image in FIG. 2B and FIG. 2C, according to certain embodiments.

DETAILED DESCRIPTION

Figure 1:
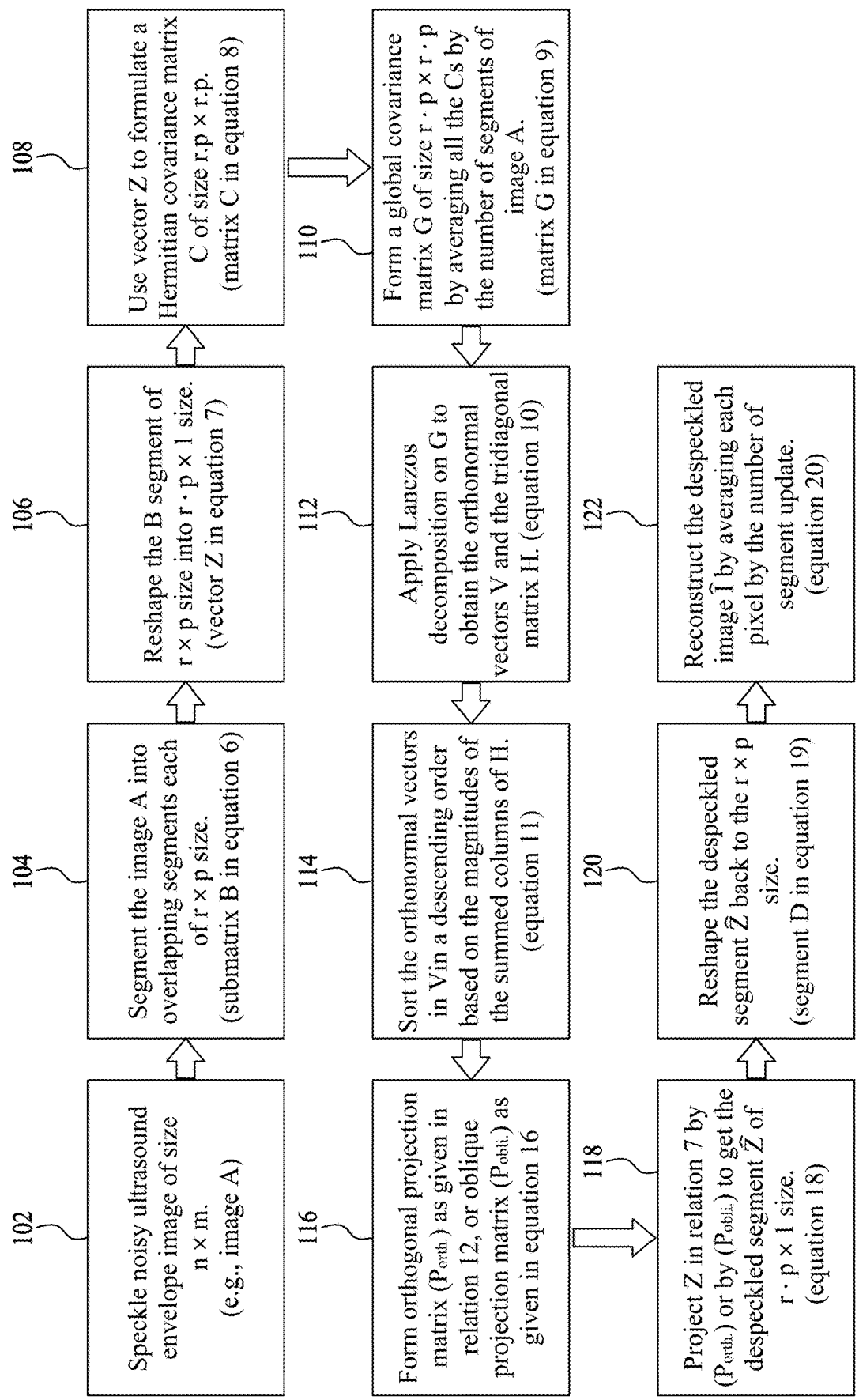
FIG. 1 is a process flow depicting steps in suppressing speckle noise in medical ultrasound images, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of current disclosure are directed to a system, device, and method for suppressing speckle noise in medical ultrasound images while maintaining low computational complexity. The medical ultrasound image is divided into overlapping subimages, and Lanczos decomposition is then applied to an average Hermitian covariance matrix of all subimages.

Resulting orthonormal vectors are used for filtering speckle noise through orthogonal and oblique projections, i.e., by projecting noisy signal onto the signal subspace. After sorting orthonormal vectors, an orthogonal projection matrix is formed by selecting first K vectors contributing to the signal, whereas an oblique projection matrix is formed by selecting the first K vectors contributing to the signal and the last K vectors contributing to the noise. The procedure of Lanczos is also followed with a singular value decomposition (SVD). Different approaches are applied to real ultrasound images and two types of speckle noise simulations: fine and rough speckle noise.

A method for suppressing speckle noise (also referred to as despeckling) in medical ultrasound images is described below.

A commonly used model for a speckle noisy image either in synthetic aperture radar (SAR) or medical ultrasound imaging is given by:

$$\psi(n,m) \approx \gamma(n,m)\Phi(n,m) + \xi(n,m), \quad (1)$$

where $\psi$ is the observed image, $\gamma$ is the noise-free image, $\Phi$ is the multiplicative noise, and $\xi$ is the additive noise. The n and m stand for axial and lateral image indices, respectively. In ultrasound imaging, the model in equation (1) can be simplified by disregarding the additive noise term. The simplified model is provided by:

$$\psi(n,m) \approx \gamma(n,m)\Phi(n,m). \quad (2)$$

The model in equation (2) can be adopted when $\psi(n, m)$ image is observed before additional preprocessing is applied including log compression and nonlinear amplification.

Matrix Decomposition is described below.

The present disclosure uses Arnoldi/Lanczos decomposition as a basis for the despeckling problem in medical ultrasound images. The Arnoldi iterative method is one of the iterative methods of linear algebra called Krylov subspace methods. The Krylov subspace is a linear subspace generated by an n-by-n matrix A and a vector b of dimension n×n spanned by the images of b under the first r powers of A (starting from $A^0=1$). The Arnoldi iterative method is useful for solving a large system of linear equations. Unlike other iterative methods, Krylov subspace methods avoid matrix-matrix operations and carry iterative approximations for all orthogonal vectors based on initial matrix-vector multiplication, thus computational cost is significantly reduced.

Let Ax=b, where $A \in C^{n \times m}$ and b is an initial vector provided to find an estimate for x, b, and $x \in C^n$. The Krylov method builds a subspace whose columns are basis vectors but not quite orthonormal, such as:

$$K_j = [b \; Ab \; A^2b \ldots A^{j-1}b]. \quad (3)$$

The Arnoldi iterative method is used to produce l independent orthonormal column vectors V from the Krylov space $K_j$, which is given as:

$$V = [v_1 \; v_2 \; v_3 \ldots v_l]. \quad (4)$$

The first orthonormal vector $v_1$ in equation (4) is produced through a Gram-Schmidt procedure where the vector b is normalized over its length such as $$v_1 = \frac{b}{\|b\|_2}.$$

The Gram-Schmidt procedure is a well-known technique used in linear algebra and numerical analysis for orthonormalizing a set of vectors in an inner product space, most commonly in Euclidean space equipped with a standard inner product.

The inverse problem where A can be retrieved is given as:

$$A = VHV^*. \quad (5)$$

The asterisk on V* denotes conjugate and H is an upper Hessenberg matrix. The H matrix is formed and built up within the Arnoldi iterative method by iteratively projecting all the previously produced and normalized orthonormal vectors $v_u$ onto the new $Av_l$, where u≤l. If A is Hermitian, then H is a tridiagonal matrix and the Arnoldi iterative method reduces to the Lanczos iterative method.

The Global Covariance Matrix is described below.

Let $B \in C^{r \times p}$ be a submatrix of the matrix A given in equation (5) and defined as B(t, s), where B (t, s) is given by:

$$B(t, s) = [a(i, j)]_{\substack{1+t \leq i \leq r+t; \\ 1+s \leq j \leq p+s}}$$

where a is an iterative parameter, $0 \leq t \leq n-r$ and $0 \leq s \leq m-p$. $0 \leq r \leq r$ and $0 \leq p \leq m$, where m and n are the size of the matrix A defined above:

$$Z(t, s) = \begin{bmatrix} a(1+t, 1+s) \\ a(1+t, 2+s) \\ \vdots \\ a(1+t, p+s) \\ a(2+t, 1+s) \\ a(2+t, 2+s) \\ \vdots \\ a(1+t, p+s) \end{bmatrix}. \quad (7)$$

For every pixel shift of t or s, a new Hermitian covariance matrix can be formed from B by reshaping it first into a column vector Z of size r·p×1 as given in equation (7).

A Hermitian covariance matrix C of size r·p×r·p is defined as:

$$C(t,s) = Z(t,s) \times Z^T(t,s), \quad (8)$$

where T indicates transposition.

A global symmetric covariance matrix G of size r·p×r·p for the whole matrix A can be calculated by averaging all covariances obtained for all pixel shifts of t or s such that:

$$G = \frac{1}{(n-r+1)(m-p+1)} \sum_{\substack{0 \leq t \leq n-r \\ 0 \leq s \leq n-r}} C(t, s). \quad (9)$$

At this point, the condition of the Lanczos iterative method in matrix decomposition is fulfilled, and Lanczos decomposition can be applied to the matrix G in Equation (9) to produce the orthonormal vector matrix V given in Equation (4) and the tridiagonal matrix H given as:

$$\underbrace{[v_1 v_2 v_3 \ldots v_{r \times p}]}_{V} \underbrace{\begin{bmatrix} \alpha_1 & \beta_1 & & & & \\ \beta_1 & \alpha_2 & \beta_2 & & & \\ & \beta_2 & \alpha_3 & & & \\ & & & \ddots & & \\ & & & & \alpha_{(x \times p)-1} & \beta_{(x \times p)-1} \\ & & & & \beta_{(x \times p)-1} & \alpha_{(x \times p)} \end{bmatrix}}_{H}, \quad (10)$$

where x×p=r×p in equation (10).

H is a symmetric tridiagonal matrix whose elements are defined as follows:

$\alpha_n = h_{nn}$, and $\beta_n = h_{n+1,n} = h_{n,n+1}$ $h_{nn} = v_n^T A v_n$ Values of alpha and beta are obtained through Lanczos iteration as follows $\beta_0 = 0$, $v_0 = 0$, b=arbitrary, $$v_1 = \frac{b}{\|b\|_2}$$

for n=1, 2, 3, ..., $u = A v_n$, $\alpha_n = v_n^T u$, $u = u - \beta_{n-1} v_{n-1} - \alpha_n v_n$, $\beta_n = \|u\|$, and $v_{n+1} = u/\beta_n$.

Orthogonal projection is described below.

The orthonormal vectors in the V matrix in Equation (10) can be sorted in descending order based on the magnitudes of the diagonal α values in H. However, for efficient sorting of the orthonormal vectors in V, the present disclosure uses sorting based on the magnitudes of the summed columns of H. The sorting operation divides the V matrix into signal subspace in $V_1$ and noise subspace in $V_2$, such as $V=[V_1][V_2]$, where:

$$V_1 = [v_1 \, v_2 \, v_3 \ldots v_k] \text{ and } V_2 = [v_{k+1} v_{k+2} \, v_{k+3} \ldots v_{r \times p}]. \quad (11)$$

In equation (11), $v_1$ is an orthonormal vector that has the largest contribution towards the signal, and $v_{r \times p}$ is the orthonormal vector that has the largest contribution towards the noise.

An orthogonal projection matrix $P_{orth}$ (P with a subscript "orth." to indicate orthogonal) is constructed from the signal subspace $V_1$ by:

$$P_{orth.} = V_1 (V_1^T V_1)^{-1} V_1^T; \quad (12)$$

where $P_{orth.}$ is symmetric ($P_{orth.}^T = P_{orth.}$) and satisfies the following conditions:

$$P_{orth.} V_1 = V_1, P_{orth.} W = 0. \quad (13)$$

In equation (13), W is the null space of the orthogonal projection and is defined by:

$$P_w = I - P_{orth.}; \quad (14)$$

where I is the identity matrix.

Another kind of projection that is not commonly used in the despeckling problem of ultrasound images is the oblique projection. Conventional orthogonal subspace projection methods are considered ineffective in suppressing speckle noise in ultrasound images because conventional methods assume that the signal and the noise are uncorrelated. Under the assumption of correlation between signal and noise, oblique subspace projection method in the beamforming stage has resulted in more accurate estimation of the ultrasound signal than does orthogonal subspace projection. In the present disclosure, it is considered that envelope image decimation (downsampling) may decrease the correlation between signal and noise. Therefore, in addition to orthogonal subspace projection, the methods of the present disclosure apply oblique subspace projection to the decimated envelope image and performs a comparison between them.

In some aspects, the nonsymmetric and the nonorthogonal projections are called oblique projections, yet the nonsymmetric and the nonorthogonal projections are idempotent, that is $E^2 = E$. Similar to orthogonal projection, the oblique projection $P_{obli.}$ (P with a subscript "obli" to indicate oblique) with a null space S satisfies the following conditions:

$$P_{obli.} V_1 = V_1, P_{obli.} S = 0. \quad (15)$$

An oblique projection $P_{obli.}$, whose signal space is $V_1$ and whose null space is S, is given as:

$$P_{obli.} = P_{orth.}(1 - S(S^T P_w S)^{-1} S^T P_w). \quad (16)$$

The null space S in equation (15) or equation (16) is placed to be at the extreme right of matrix $V_2$ in equation (11) as follows:

$$S = [v_{r \times p - k + 1} v_{r \times p - k + 2} v_{r \times p - k + 3} \ldots v_{r \times p}]; \quad (17)$$

The number of orthonormal vectors in $V_1$ and in S is the same, with an in-between guard band of $r \times p - 2 \times k$ orthonormal vectors.

To perform speckle noise suppression, $P_{orth.}$ in equation (12) or $P_{obli.}$ in equation (16) can be used to project the speckle noisy signal onto the signal subspace where the estimated vector signal $\hat{Z}$ of size r·p×1 in equation (7) is given as:

$$\hat{Z}(t,s) = P \times Z(t,s) = \begin{bmatrix} \hat{z}_1^{(t,s)} \\ \hat{z}_2^{(t,s)} \\ \vdots \\ \hat{z}_{rp}^{(t,s)} \end{bmatrix}; \quad (18)$$

where P indicates either $P_{orth.}$ or $P_{obli.}$. The estimated vector $\hat{Z}$ is reshaped back into r×p segment D by:

$$D(t,s) = \begin{bmatrix} \hat{z}_1^{(t,s)} & \hat{z}_2^{(t,s)} & \vdots & \hat{z}_p^{(t,s)} \\ \hat{z}_{p+1}^{(t,s)} & \hat{z}_{p+2}^{(t,s)} & \vdots & \hat{z}_{2p}^{(t,s)} \\ \vdots & \vdots & \ddots & \vdots \\ \hat{z}_{rp-p+1}^{(t,s)} & \hat{z}_{rp-p+2}^{(t,s)} & \ldots & \hat{z}_{rp}^{(t,s)} \end{bmatrix} = [d_{(i,j)}^{(t,s)}]_{\substack{1 \le i \le r \\ 1 \le j \le p}}. \quad (19)$$

The estimated image $\hat{I}$ can be reconstructed by averaging each pixel by the number of segment updates, as follows:

$$\hat{I} = \left[ \frac{\sum_{x=0}^{i} \sum_{y=0}^{j} d_{(x,y)}^{(1-x,j-y)}}{i \times j} \right]_{\substack{1 \le i \le n \\ 1 \le j \le m}}; \quad (20)$$

The above aspect speckle noise suppression is summarized in FIG. 1 as a process flow that is described below.

FIG. 1 is a process flow depicting steps in suppressing speckle noise in medical ultrasound images, according to one or more embodiments.

Step 102 includes receiving a speckle noisy n×m ultrasound envelope image matrix A formed by a plurality of pixels of an medical ultrasound image.

Step 104 includes segmenting the n×m ultrasound envelope image matrix A into a number of overlapping segments of r×p size, to form a sub-matrix B (as described in equation 6) for each overlapping segment. The n is an axial image index, m is a lateral image index, where 0≤r≤n and 0≤p≤m.

Step 106 includes reshaping each sub-matrix B into a column vector Z (as described in equation 7) of size r·p×1;

Step 108 includes formulating a Hermitian covariance matrix C of size r·p×r·p from the column vectors Z (as described in equation 8).

Step 110 includes forming a global covariance matrix G of size r·p×r·p by averaging the Hermitian covariance matrices C by the number of overlapping segments of the image matrix A (as described in equation 9).

Step 112 includes applying Lanczos decomposition to the global covariance matrix G to generate an orthonormal vector matrix V composed of orthonormal vectors, v and a tridiagonal matrix H (as described in equation 10). Further each column of the tridiagonal matrix H is summed to obtain a magnitude of each column.

Step 114 includes sorting the orthonormal vectors, v, of orthonormal vector matrix V in descending order based on the magnitude of each column (as described in equation 11). The sorting the orthonormal vectors divides the orthonormal vector matrix V into a signal subspace $V_1$ and a noise subspace $V_2$.

Step 116 includes forming an orthogonal projection matrix $P_{orth}$ from a first subset of the orthonormal vectors of signal subspace $V_1$, or forming an oblique projection matrix $P_{obli.}$ from the orthonormal vectors V by subtracting each noise subspace $V_2$ from orthonormal vector matrix V (as described in equation 16).

Step 118 includes projecting Z by $P_{orth.}$ or by $P_{obli.}$ for each sub-matrix B to get an estimated vector signal $\hat{Z}$ of size r·p×1 (as described in equation 18) and forming an estimated despeckled segment D of size r×p from the estimated vector signal $\hat{Z}$ (as described in equation 18).

Step 120 includes forming or reshaping an estimated despeckled segment D of size r×p from the estimated vector signal $\hat{Z}$ (as described in equation 19).

Step 122 includes reconstructing an estimated despeckled ultrasound image $\hat{I}$ by averaging each pixel of the plurality of pixels by the number of segment updates (as described in equation 20). The estimated despeckled ultrasound image $\hat{I}$ may be rendered on the display of the computing device.

To assess the quality of the despeckled medical ultrasound images, different assessing measures may be considered. Let $I_{ref}$ be a reference image and $I_{est}$ be an estimated image, signal-to-noise ratio (SNR) is defined as:

$$SNR = E\left\{ \frac{\|I_{ref}\|_F}{\|I_{ref} - I_{est}\|_F} \right\}, \quad (21)$$

where $\|.\|_F$ is a Frobenius norm, and E{.}, is an expectation.

Peak signal-to-noise ratio (PSNR), on the other hand, is widely used to measure how close two images are to each other, given as $$PSNR = E\left\{ \frac{\max|I_{ref}|^2}{\|I_{ref} - I_{est}\|_F} \right\}. \quad (22)$$

Besides SNR and PSNR measurement, measurements may be of decibels (dB) as known in the area of image processing and measurements of the despeckling area of medical ultrasound images, such as edge detection β are made:

$$\beta = E\left\{ \frac{\langle \Delta I_{ref}, \Delta I_{est} \rangle}{\|I_{ref}\|_F \|I_{est}\|_F} \right\}, \quad (23)$$

where Δ is the Laplacians operator and ⟨.⟩ is the standard inner product. The closeness of β to 1 is an indication of the accuracy of the edge detection.

A resolution assessing measure α which indicates resolution is widely used to assess the resolution in medical ultrasound images. The lower the value of α, the more accurate the resolution of the image. If ψ=

$$R_{I_{est}I_{est}}$$

$(\tau_n, \tau_m)$ is the estimated autocorrelation function of an image, where $\tau_n$ and $\tau_m$ are the lags in n and m indices, then α (alpha, not to be confused with "α" of equation (7)) is defined as:

$$\alpha = \frac{\sum_{(i,j)=(1,1)}^{(n,m)} \left( |\Psi|^{(i,j)} \ge .75 \times \max|\Psi| \right)}{n \times m}. \quad (24)$$

Contrast-to-noise ratio (CNR) is a common assessment measurement in medical applications. The CNR is an absolute difference in the SNR of two different regions within the image:

$$CNR = \frac{|S_A - S_B|}{\sigma_N}, \quad (25)$$

where $S_A$, $S_B$, and $\sigma_N$ are signal of region A, signal of region B, and standard deviation of background noise, respectively.

Speckle signal-to-noise ratio (S-SNR) is a common assessing measure in medical ultrasound images. The S-SNR is defined as the mean to the standard deviation of the image of interest. The S-SNR is a measure of the fluctuation of speckle, and the higher the value of S-SNR indicates a better quality of the despeckled image.

Another assessment measure used in the quality evaluation of medical images is the feature similarity (FSIM) index, given as:

$$FSIM = \frac{\sum_{x \in \Omega} S_L(X).PC_m(X)}{\sum_{x \in \Omega} PC_m(X)}; \quad (26)$$

where $\Omega$ is the spatial domain and $S_L(X)$ is the similarity measure at each location X within the image. $PC_m(X)$=max $(PC_1, PC_2)$ is the maximum phase congruency of the two phase congruencies at each location X within the reference image $I_{ref}$ and the estimated image $I_{est}$, respectively. The closer FSIM is to 1, the higher the image quality.

A mean structural similarity (MSSIM) index is an overall quality measure of luminance, contrast, and structure. The structural similarity (SSIM) index uses these parameters in assessing the quality of an image, where MSSIM is given by:

$$MSSIM = \frac{1}{N_w} \sum_{k=1}^{N_w} SSIM(I_{ref}^i, I_{est}^i), \quad (27)$$

where $N_w$ is the number of local windows. The $I_{ref}$ and $I_{est}$ are the subimages of the i'th local window. The closer MSSIM is to 1, the higher the image quality.

To test the validity of Lanczos decomposition in the despeckling problem of ultrasound images, a disc consisting of different geometrical shapes including sharp edges and curves was simulated through field II program. The field II program is an open source program for simulating ultrasound transducer fields and ultrasound imaging using linear acoustics offered by Jørgen Arendt Jensen. The field II program is capable of calculating the emitted and pulse-echo fields for both the pulsed and continuous wave case for a large number of different transducers. The field II program is capable of simulating any kind of linear imaging as well as realistic images of a tissue.

An ultrasound device typically includes a transducer, a transmitter pulse generator, one or more compensating amplifiers, a control unit for focusing, one or more digital processors and one or more systems for display. It is used in cases of abdominal, cardiac, gynecological, urological and cerebrovascular examination, breast examination, and the like. The term "ultrasound" applies to all acoustic energy with a frequency above human hearing (20,000 hertz or 20 kilohertz). Typical diagnostic sonographic scanners operate in the frequency range of 2 to 18 megahertz, hundreds of times greater than the limit of human hearing. Higher frequencies (e.g., 6 to 18 megahertz, 10 to 18 megahertz or 12 to 18 megahertz) have a correspondingly smaller wavelength, and can be used to make sonograms with smaller details. Diagnostic sonography (ultrasonography) is an ultrasound-based diagnostic imaging technique used to visualize subcutaneous body structures including tendons, muscles, joints, vessels and internal organs for possible pathology or lesions. Sonography is effective for imaging soft tissues of the body. Sonographers typically use a hand-held probe (called a transducer) that is placed directly on and moved over the patient. A water-based gel is typically used to couple the ultrasound between the transducer and patient.

Reflection technology (echo) is typically used to register a pulse reflected from the boundary of two tissues with different acoustic resistance. The sound wave is typically produced by a piezoelectric transducer encased in a probe. Strong, short electrical pulses from the ultrasound machine make the transducer emit at the desired frequency. The resulting ultrasound emission can be focused either by the shape of the transducer, a lens in front of the transducer, or a complex set of control pulses from the ultrasound scanner machine to produce an arc-shaped sound wave from the face of the transducer. Phased array techniques permit the sonographic machine to change the direction and depth of focus.

A transducer may be swept mechanically by rotating or swinging to generate a 2 D-image or 3 D image. Received sound is processed and used to construct an image which represents a slice or section of the body of the patient. 3D images can be generated by acquiring a series of adjacent 2D images.

Four different modes of ultrasound are used in medical imaging. These are:

A-mode: the simplest type of ultrasound. A single transducer scans a line through the body with the echoes plotted on screen as a function of depth. Therapeutic ultrasound aimed at a specific tumor or calculus is also A-mode, to allow for pinpoint accurate focus of the destructive wave energy.

B-mode: a linear array of transducers simultaneously scans a plane through the body that can be viewed as a two-dimensional image on screen.

M-mode: in m-mode a rapid sequence of B-mode scans whose images follow each other in sequence on screen enables doctors to see and measure range of motion, as the organ boundaries that produce reflections move relative to the probe.

Doppler mode: makes use of the Doppler effect in measuring and visualizing blood flow. Doppler sonography play important role in medicine. Sonography can be enhanced with Doppler measurements, which employ the Doppler effect to assess whether structures (usually blood) are moving towards or away from the probe, and its relative velocity. By calculating the frequency shift of a particular sample volume, for example a jet of blood flow over a heart valve, its speed and direction can be determined and visualized. This is particularly useful in cardiovascular studies (sonography of the vasculature system and heart) and essential in many areas such as determining reverse blood flow in the liver vasculature in portal hypertension. The Doppler information is displayed graphically using spectral Doppler, or as an image using color Doppler (directional Doppler) or power Doppler (non directional Doppler). This Doppler shift falls in the audible range and is often presented audibly using stereo speakers: this produces a very distinctive, although synthetic, pulsing sound.

A medical ultrasound transducer (echo scopic probe) is a device that is placed on the patient's body and contains one or more ultrasonic transducers and may include: linear probe, sectoral probe, a probe in which the ring changer focusing is performed in a rocking mirror test, with a convex probe.

Figure 2A:
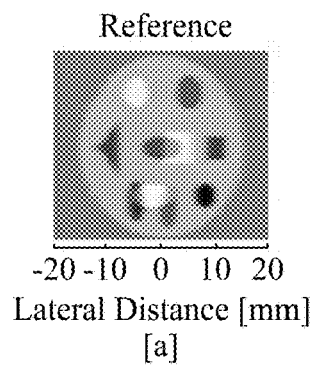
FIG. 2A is a reference ultrasound image, according to certain embodiments.

The ultrasound image shown in FIG. 2A was made of 256 radio frequency lines (RF lines) with a width of 40 mm. The RF lines through Hanning apodization for transmission and reception were produced through the use of a 192 element transducer with 64 active elements. The center frequency was set to 3.5 MHz and the sampling frequency was set to 100 MHz. The width of each element was set to 5 mm and the kerf between elements was kept to 0.05 mm. A fixed focal point was placed at 70 mm and echoes were received at 20 mm intervals starting from 30 mm from the transducer surface. Each of the 256 echoes of 4096 samples was envelope detected through Hilbert transform and then decimated by a factor of 16 to produce the image in FIG. 2A of size 256×256.

Figure 2B:
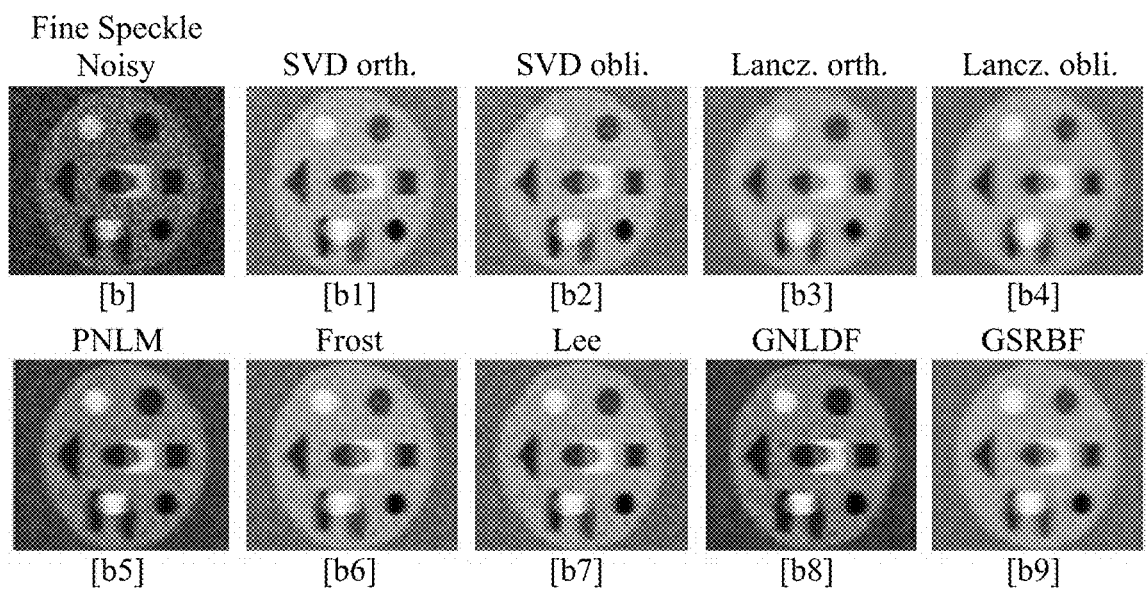
FIG. 2B illustrates a visual performance of despeckling approaches applied to a fine (F) speckle noise simulation, according to certain embodiments.
Figure 2C:
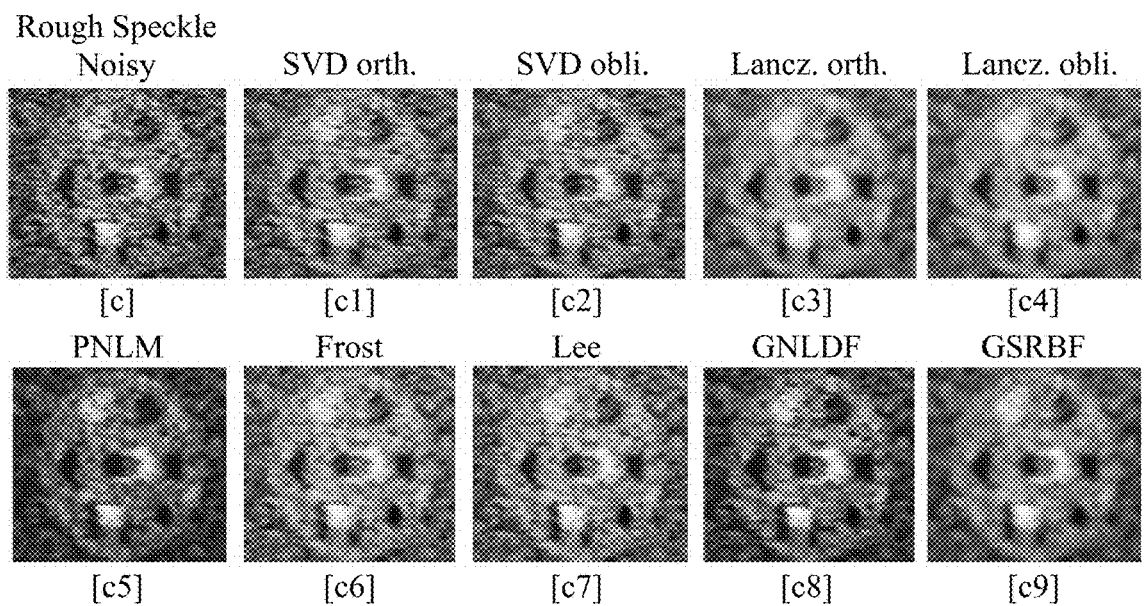
FIG. 2C illustrates a visual performance of despeckling approaches applied to a rough (R) speckle noise simulation, according to certain embodiments.

The simulation is performed in two phases: the fine speckle noisy images shown in FIG. 2B and the rough speckle noisy images shown in FIG. 2C The fine speckle noisy image is produced by multiplying the envelope image before decimation with a Gaussian noise N(0, 1). For the rough speckle noisy image, 90,000 scatterers were randomly distributed throughout the phantom image before it was scanned by field II simulating program. Ten independent random distributions of the scatterers are made and for each one field II is run. The same parameters of scanning described above are used for both types of simulation.

FIG. 2B illustrates a visual performance of despeckling approaches applied to a fine (F) speckle noise simulation, according to certain embodiments. FIG. 2B includes an image [b] illustrating a fine speckle noise image, an image [b1] illustrating a visual performance of the SVD orthogonal despeckling approach on the image of FIG. 2A, an image [b2] illustrates a visual performance of a SVD oblique despeckling approach the image of FIG. 2A, an image [b3] illustrates a visual performance of a Lanczos orthogonal despeckling approach on the image of FIG. 2A, an image [b4] illustrates a visual performance of Lanczos oblique despeckling approach on the image of FIG. 2A, an image [b5] illustrates a visual performance of a probabilistic non local means (PNLM) despeckling approach on the image of FIG. 2A, an image [b6] illustrates a visual performance of a Frost despeckling approach on the image of FIG. 2A, an image [b7] a visual performance of a Lee despeckling approach on the image of FIG. 2A, an image [b8] illustrates a visual performance of a geometric nonlinear diffusion filter (GNLDF) despeckling approach on the image of FIG. 2A, and an image [b9] illustrates a visual performance of a guided speckle reducing bilateral filter (GSRBF) despeckling approach on the image of FIG. 2A.

FIG. 2C illustrates a visual performance of despeckling approaches applied to a rough (R) speckle noise simulation, according to certain embodiments. FIG. 2C includes an image [c] illustrating a rough speckle noise image, an image [c1] illustrating a visual performance of a SVD orthogonal despeckling approach on the image of FIG. 2A, an image [c2] illustrates a visual performance of the SVD oblique despeckling approach on the image of FIG. 2A, an image [c3] illustrates a visual performance of the Lancz orthogonal despeckling approach on the image of FIG. 2A, an image [c4] illustrates a visual performance of the Lanczos oblique despeckling approach on the image of FIG. 2A, an image [c5] illustrates a visual performance of the PNLM orthogonal despeckling approach on the image of FIG. 2A, an image [c6] illustrates a visual performance of the Frost despeckling approach on the image of FIG. 2A, an image [c7] a visual performance of the Lee despeckling approach on the image of FIG. 2A, an image [c8] illustrates a visual performance of the GNLDF despeckling approach on the image of FIG. 2A, and an image [c9] illustrates a visual performance of the GSRBF despeckling approach on the image of FIG. 2A. FIG. 2B and FIG. 2C are subjected to orthogonal and oblique Lanczos despeckling to form an orthogonal projection matrix $P_{orth.}$ from a first subset of the orthonormal vectors of signal subspace $V_1$ and an oblique projection matrix $P_{obli.}$ from the first subset of the orthonormal vectors of signal subspace $V_1$ with a null space S. As an eigen-based benchmark decomposition scheme, the same orthogonal and oblique despeckling approach was followed except by replacing Lanczos decomposition with the SVD. The Lanczos despeckling approach of the disclosure is also tested against benchmark despeckling approaches that are usually used in the despeckling area of ultrasound images, such as the PNLM despeckling approach, the GNLDF despeckling approach, the GSRBF despeckling approach, and the Frost despeckling approach and the Lee despeckling approach. These benchmark despeckling approaches are known in the art and are not explained herein for the sake of conciseness and brevity. Visual despeckling results for all despeckling approaches are shown in FIG. 2B and FIG. 2C. Labels are provided above the images in FIG. 2B and FIG. 2C to provide ease of understanding. FIG. 2B illustrates a visual performance of despeckling approaches applied to a fine (F) speckle noise simulation, and FIG. 2C illustrates a visual performance of despeckling approaches applied to a rough (R) speckle noise simulation.

The despeckling parameters of various despeckling approaches used in this study are presented in Table 1. In Table 1, parameters include patch size (p.size), search window (s.win.), correction parameter (c.para.), window size (w.size), Iteration (iter.), diffusion (diff.), spatial similarity (sig. —s), and range similarity (sig. —r). The proper domain (Dom.) of the despeckling column in Table 1 indicates the domain in which each despeckling approach performs the best. To provide best possible numerical results with a minimum degree of image blur, parameters are tuned and adjusted for the simulated fine and rough speckle noise experiments of FIG. 2B and FIG. 2C, as denoted in Table 1 by F and R, respectively. The SVD is used with the same despeckling parameters as the Lanczos despeckling approach, to assess the difference of performance between both despeckling approach.

TABLE 1

Despeckling parameters of despeckling approach.

| Despeckling approach | F | R | Kidney | Liver | Lymph node | Dom. |
|---|---|---|---|---|---|---|
| SVD |  |  |  |  |  | Spat. |
| r × p | 8 × 8 | 8 × 8 | 8 × 8 | 8 × 8 | 8 × 8 |  |
| k | 4 | 4 | 4 | 4 | 4 |  |
| Lanczos |  |  |  |  |  | Spat. |
| r × p | 8 × 8 | 8 × 8 | 8 × 8 | 8 × 8 | 8 × 8 |  |
| k | 4 | 4 | 4 | 4 | 4 |  |
| PNLM |  |  |  |  |  | Log |
| p. size | 3 | 3 | 3 | 3 | 3 |  |
| s. win. | 5 | 7 | 7 | 5 | 7 |  |
| c. para. | 1 | 1 | 1 | 1 | 1 |  |
| Frost |  |  |  |  |  | Spat. |
| w. size | 5 | 7 | 7 | 5 | 7 |  |
| Lee |  |  |  |  |  | Spat. |
| w. size | 3 | 3 | 3 | 3 | 3 |  |
| # of iter. | 3 | 5 | 3 | 3 | 4 |  |

TABLE 1-continued

Despeckling parameters of despeckling approach.

| Despeckling approach | F | R | Kidney | Liver | Lymph node | Dom. |
|---|---|---|---|---|---|---|
| GNLDF | | | | | | Log |
| diff. | 0.25 | 0.25 | 0.25 | 0.25 | 0.25 | |
| # of iter. | 30 | 35 | 30 | 30 | 30 | |
| Region | Wide | Wide | Wide | Wide | Wide | |
| GSRBF | | | | | | Spat. |
| w. size | 5 | 7 | 7 | 7 | 7 | |
| sig.- s | 12 | 12 | 12 | 12 | 12 | |
| sig.- r | 70 | 70 | 70 | 70 | 70 | |

Table 2 lists the numerical results as an average of 50 independent trials for the fine speckle noise experiment. The table also lists the numerical results as an average of 10 independent trials for the rough speckle noise experiment. The numbers in parentheses in Table 2 are the rank in the descending order, except for Alpha in the ascending order. Table 2 also includes an average (Avg.) rank (a to h) for all assessing methods. The rank is used to better assess the despeckling approaches.

TABLE 2

Numerical performance of despeckling approaches for fine (F) and rough (R) speckle noise simulation.

| Method | | Alpha a | | CNR b | | S-SNR c | | SNR dB d | | PSNR dB e | | Beta f | | FSIM g | | MSSIM h | | Avg. rank a to h | |
|---|---|---|---|---|---|---|---|---|---|---|---|---|---|---|---|---|---|---|---|
| Simulated | F | 0.00012 | | 0.196 | | 1.147 | | 3.368 | | 16.167 | | 0.120 | | 0.637 | | 0.314 | | — | |
| noise image. | R | 0.003 | | 0.166 | | 1.125 | | 4.960 | | 17.307 | | 0.070 | | 0.633 | | 0.340 | | — | |
| SVD orth. | F | 0.075 | 3 | 0.132 | 4 | 1.950 | 3 | 17.855(5) | | 28.96 | 6 | 0.206 | 3 | 0.903 | 5 | 0.858 | 5 | 4.250 | 6 |
| | R | 0.013 | 1 | 0.145 | 4 | 1.306 | 6 | 6.843(7) | | 18.820 | 7 | 0.071 | 3 | 0.693 | 7 | 0.441 | 7 | 5.250 | 6 |
| SVD obli. | F | 0.075 | 3 | 0.132 | 4 | 1.950 | 3 | 17.855(5) | | 28.963 | 6 | 0.206 | 3 | 0.903 | 5 | 0.858 | 5 | 4.250 | 6 |
| | R | 0.013 | 1 | 0.145 | 4 | 1.306 | 6 | 6.843(7) | | 18.820 | 7 | 0.071 | 3 | 0.693 | 7 | 0.441 | 7 | 5.250 | 6 |
| Lanczos orth. | F | 0.080 | 4 | 0.148 | 1 | 2.196 | 1 | 21.907(2) | | 30.837 | 1 | 0.220 | 2 | 0.927 | 2 | 0.910 | 2 | 1.875 | 1 |
| | R | 0.084 | 7 | 0.136 | 5 | 1.585 | 3 | 13.758(1) | | 23.671 | 1 | 0.068 | 5 | 0.851 | 2 | 0.665 | 2 | 3.250 | 2 |
| Lanczos obli. | F | 0.082 | 5 | 0.148 | 1 | 2.196 | 1 | 22.172(1) | | 30.826 | 2 | 0.220 | 2 | 0.927 | 2 | 0.910 | 2 | 2.000 | 2 |
| | R | 0.084 | 7 | 0.136 | 5 | 1.585 | 3 | 13.758(1) | | 23.671 | 1 | 0.068 | 5 | 0.851 | 2 | 0.665 | 2 | 3.250 | 2 |
| PNLM | F | 0.041 | 1 | 0.140 | 2 | 2.008 | 2 | 20.404(2) | | 28.980 | 5 | 0.178 | 6 | 0.893 | 6 | 0.856 | 6 | 3.750 | 4 |
| | R | 0.015 | 2 | 0.166 | 1 | 1.604 | 1 | 8.919(5) | | 20.420 | 5 | 0.062 | 6 | 0.720 | 6 | 0.546 | 5 | 3.870 | 4 |
| Frost | F | 0.080 | 4 | 0.139 | 3 | 1.643 | 7 | 19.486(3) | | 29.799 | 3 | 0.182 | 5 | 0.908 | 3 | 0.874 | 3 | 3.875 | 5 |
| | R | 0.054 | 5 | 0.148 | 3 | 1.406 | 5 | 9.749(4) | | 21.017 | 4 | 0.071 | 2 | 0.789 | 3 | 0.551 | 4 | 3.750 | 3 |
| Lee | F | 0.075 | 3 | 0.148 | 1 | 1.603 | 8 | 17.256(6) | | 28.309 | 7 | 0.148 | 7 | 0.876 | 7 | 0.843 | 7 | 5.750 | 8 |
| | R | 0.043 | 4 | 0.151 | 2 | 1.349 | 6 | 8.646(6) | | 20.175 | 6 | 0.069 | 4 | 0.759 | 5 | 0.511 | 6 | 4.875 | 5 |
| GNLDF | F | 0.045 | 2 | 0.122 | 5 | 1.946 | 4 | 18.033(5) | | 27.671 | 8 | 0.196 | 4 | 0.907 | 4 | 0.869 | 4 | 4.500 | 7 |
| | R | 0.024 | 3 | 0.125 | 6 | 1.591 | 2 | 10.478(3) | | 21.299 | 3 | 0.079 | 1 | 0.786 | 4 | 0.588 | 3 | 3.125 | 1 |
| GSRBF | F | 0.089 | 6 | 0.105 | 6 | 1.676 | 6 | 18.731(4) | | 29.473 | 4 | 0.230 | 1 | 0.939 | 1 | 0.917 | 1 | 3.625 | 3 |
| | R | 0.083 | 6 | 0.104 | 7 | 1.553 | 4 | 11.576(2) | | 22.621 | 2 | 0.072 | 2 | 0.866 | 1 | 0.709 | 1 | 3.125 | 1 |

Visually, Lanczos orthogonal image [b3], Lanczos oblique image [b4], and GSRBF image [b9] in FIG. 2B, have shown maximum cleaning of the fine speckle noise. The same performance can also be seen in Lanczos orthogonal image [c3], Lanczos oblique image [c4], and GSRBF image [c9] in FIG. 2C for rough speckle noise.

Figure 3A:
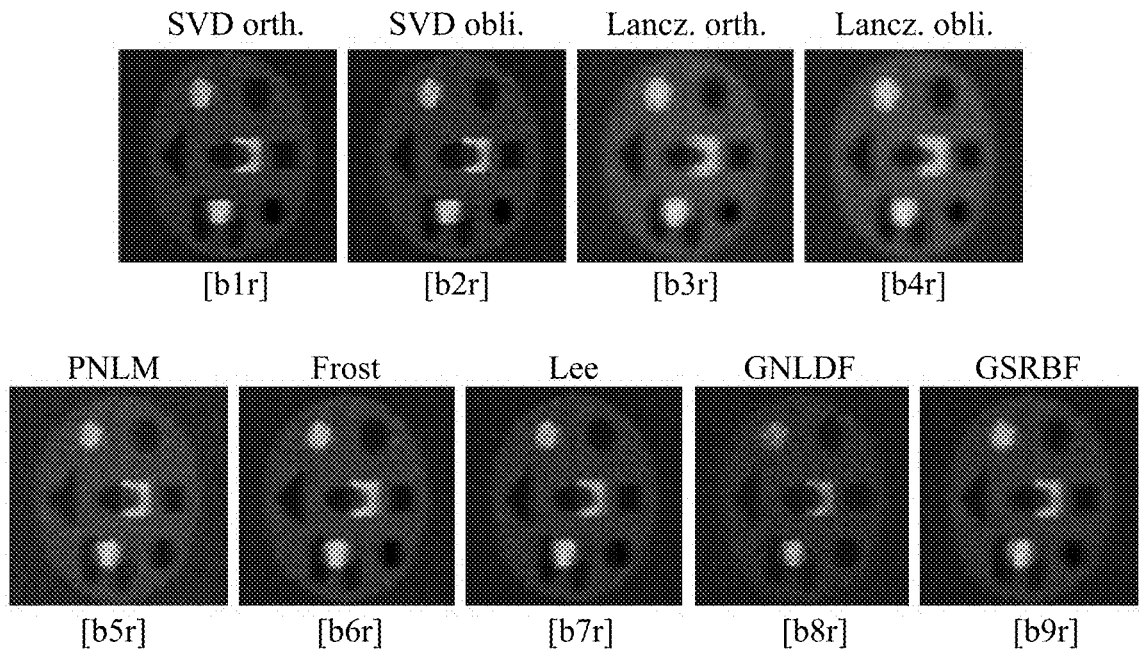
FIG. 3A illustrates residual images of despeckling approaches as a difference between the fine speckle noise images of FIG. 2B and a despeckled image, according to certain embodiments.
Figure 3B:
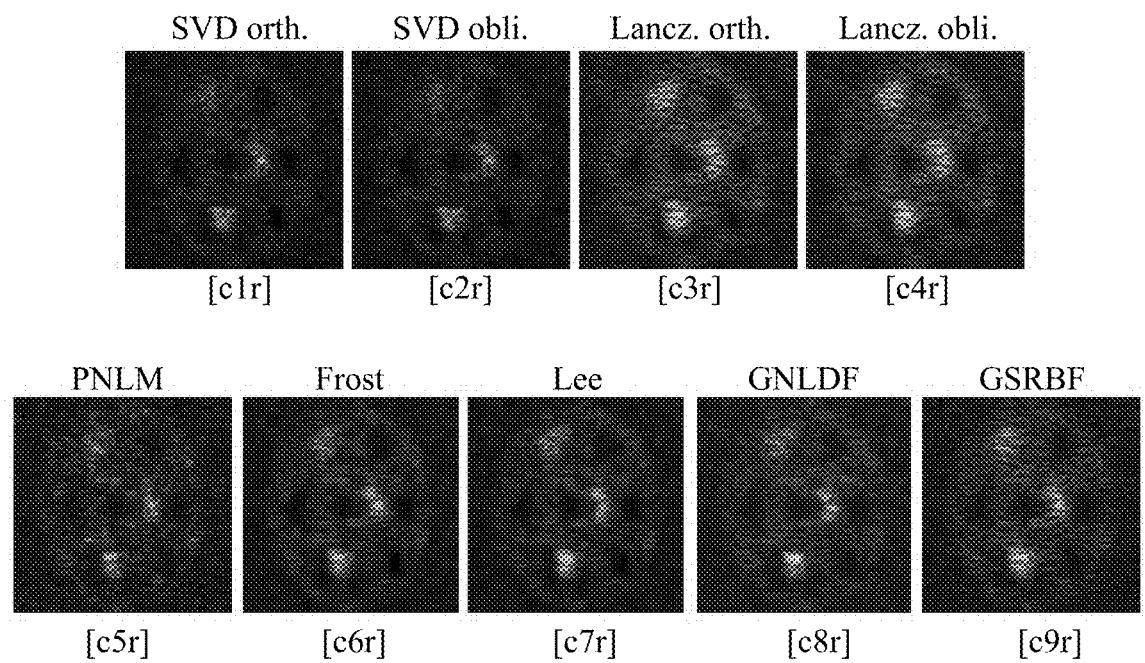
FIG. 3B illustrates residual images of despeckling approaches as a difference between the rough speckle noise image of FIG. 2C and a despeckled image, according to certain embodiments.

FIG. 3A and FIG. 3B show the residual images of the despeckling approaches described above. FIG. 3A illustrates residual images of despeckling approaches as a difference between the fine speckle noise images of FIG. 2B and a despeckled image, according to certain embodiments. FIG. 3A includes an image [b1r] illustrating the residual image obtained by applying the SVD orthogonal despeckling approach, an image [b2r] illustrates a residual image obtained by applying the SVD oblique despeckling approach, an image [b3r] illustrates a residual image obtained by applying the Lancz orthogonal despeckling approach on image, image [b4r] illustrates a residual image obtained by applying the Lanczos oblique despeckling approach, image [b5r] illustrates a residual image obtained by applying the PNLM despeckling approach, image [b6r] illustrates a residual image obtained by applying the Frost despeckling approach on image of FIG. 2B, image [b7r] illustrates a residual image obtained by applying the Lee despeckling approach on image of FIG. 2C, image [b8r] illustrates a residual image obtained by applying the GNLDF despeckling approach, and image [b9r] illustrates a residual image obtained by applying the GSRBF despeckling approach.

FIG. 3B illustrates residual images of despeckling approaches as a difference between the rough speckle noise image of FIG. 2C and a despeckled image, according to certain embodiments. FIG. 3B includes image [c1r] that illustrates a residual image obtained using the SVD orthogonal despeckling approach, image [c2r] illustrates a residual image obtained using the SVD oblique despeckling scheme, image [c3r] illustrates a residual image obtained using the Lancz orthogonal despeckling approach, image [c4r] illustrates a residual image obtained using the Lanczos oblique despeckling approach, image [c5r] illustrates a residual image obtained using the PNLM despeckling approach, image [c6r] illustrates a residual image obtained using the Frost despeckling approach, image [c7r] illustrates a residual image obtained using the Lee despeckling approach on image of FIG. 2C, image [c8r] illustrates a residual image obtained using the GNLDF despeckling approach, and image [c9r] illustrates a residual image obtained using the GSRBF despeckling approach.

The residual image represents the difference between the speckle noisy image and the despeckled image and illustrates how much speckle noise is removed. Since speckle noise obstructs the structure in varying degrees, residual image can be reviewed at as a skinned off distorting noisy layer. For example, based on FIG. 2A and FIG. 2B, the GSRBF despeckling approach appears to be more efficient than the PNLM despeckling approach in suppressing speckle noise. This observation is clear in the residual images of FIG. 3A and FIG. 3B, where the GSRBF despeckling approach removes more speckle noise than the PNLM despeckling approach as seen in image [b9r] of FIG. 3A, when compared to image [b5r] of FIG. 3A for fine speckle noise, and more clearly seen in image [c9r] of FIG. 3B when compared with image of [c5r] of FIG. 3B for rough speckle noise. A similar observation applies to Lanczos (orthogonal or oblique) when compared with the GNLDF despeckling approach for either speckle noise simulation, where the Lanczos despeckling approach is found more efficient than the GNLDF despeckling approach in skinning off the speckle noisy layer. An interesting observation the residual images have provided is the behavior of SVD despeckling process. Different from the Lanczos with either projection (orthogonal or oblique) and different from the efficiency of the Lanczos in removing fine and rough speckle noise (large speckle clusters), SVD, on the other hand, with either projection is found limited to suppressing fine speckle noise, or the fine speckle noise found among the larger speckle noise clusters. This limited ability of SVD can be clearly seen in the residual images of [c1r] of FIG. 3B and image [c2r] of FIG. 3B, when compared with the Lanczos in image [c3r] and [c4r] of FIG. 3B.

Figure 4A:
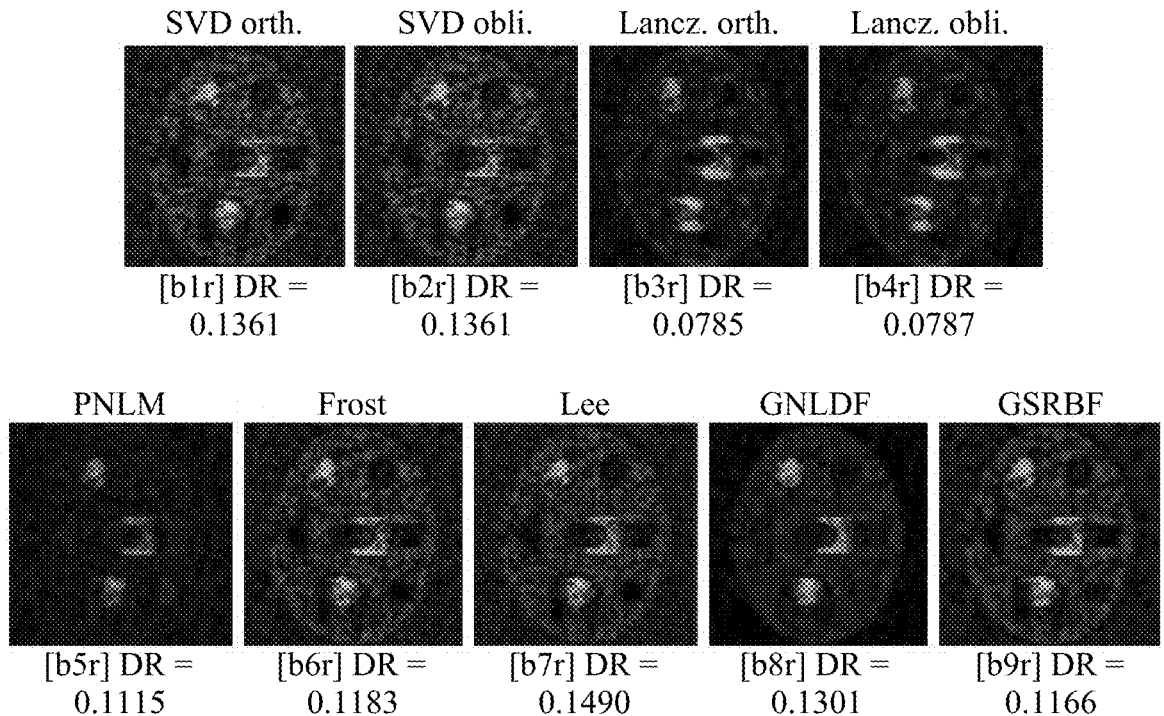
FIG. 4A illustrates residual images of despeckling approaches as a difference between a noise-free original image of FIG. 2A and a despeckled image, according to certain embodiments.
Figure 4B:
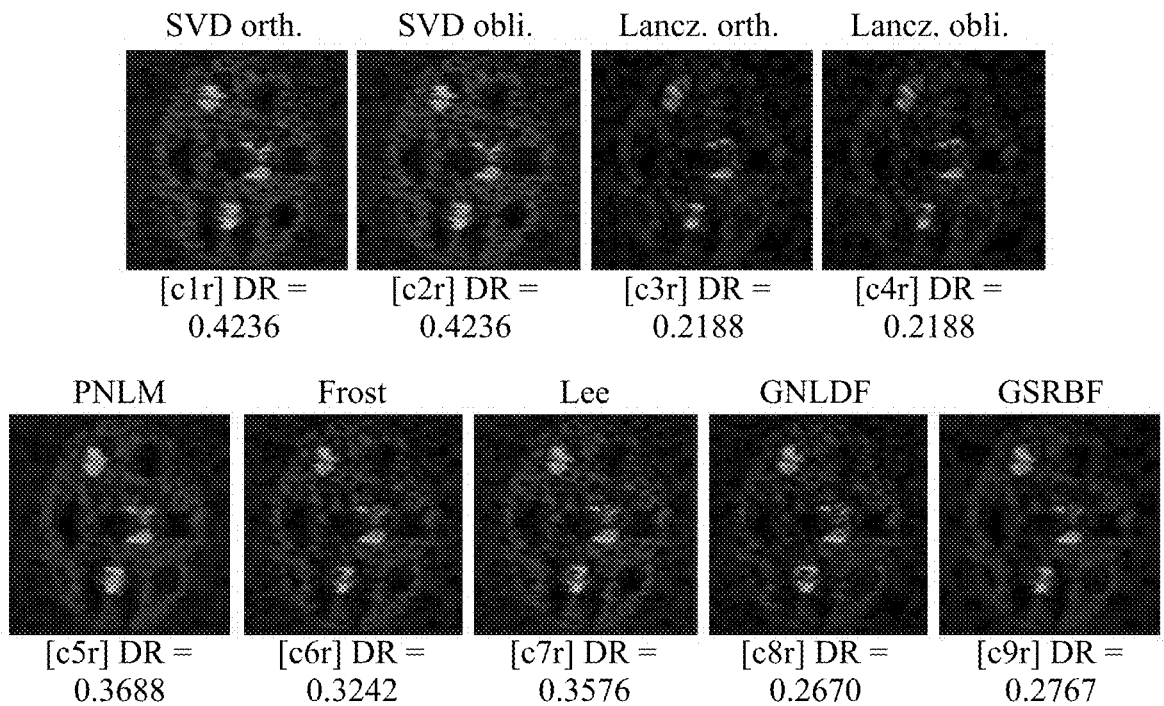
FIG. 4B illustrates residual images of despeckling approaches as a difference between the noise-free original image of FIG. 2A and a despeckled image, according to certain embodiments.

FIG. 4A and FIG. 4B correspond to FIG. 2A and FIG. 3B (respectively) and FIG. 3A and FIG. 3B (respectively), further demonstrate that the residual image shows the skinned off speckle noisy layer that obstructs the structure. FIG. 4A and FIG. 4B demonstrate the difference between the noise-free image and the despeckled image.

FIG. 4A illustrates residual images of despeckling approaches as a difference between a noise-free original image of FIG. 2B and a despeckled image, according to certain embodiments. FIG. 4A includes image [b1r] illustrating the residual image obtained from the SVD orthogonal despeckling approach with a difference ratio (DR)=0.1361, image [b2r] illustrates a residual image obtained using the SVD oblique despeckling approach with a DR=0.1361, image [b3r] illustrates a residual image obtained using the Lancz orthogonal despeckling approach with a DR=0.0785, image [b4r] illustrates a residual image obtained using the Lanczos oblique despeckling approach with a DR=0.0787, image [b5r] illustrates a residual image obtained using the PNLM despeckling approach with a DR=0.1115, image [b6r] illustrates a residual image obtained using the Frost despeckling approach with a DR=0.1183, image [b7r] illustrates a residual image obtained using the Lee despeckling approach with a DR=0.1490, image [b8r] illustrates a residual image obtained using the GNLDF despeckling approach with a DR=0.1301, and image [b9r] illustrates a residual image obtained using the GSRBF despeckling approach with a DR=0.1166.

FIG. 4B illustrates residual images of despeckling approaches as a difference between the noise-free original image of FIG. 2C and a despeckled image, according to certain embodiments. FIG. 4B includes image [c1r] that illustrates a residual image obtained using the SVD orthogonal despeckling approach on image of FIG. 2C with a DR=0.4236, image [c2r] illustrates a illustrates a residual image obtained using the SVD oblique despeckling approach with a DR=0.4236, image [c3r] illustrates a residual image obtained using the Lancz orthogonal despeckling approach with a DR=0.2188, image [c4r] illustrates a residual image obtained using the Lanczos oblique despeckling approach with a DR=0.2188, image [c5r] illustrates a residual image obtained using the PNLM despeckling approach with a DR=0.3688, image [c6r] illustrates a residual image obtained using the Frost despeckling approach a DR=0.3242, image [c7r] illustrates a residual image obtained using the Lee despeckling approach a DR=0.3576, image [c8r] illustrates a residual image obtained using the GNLDF despeckling approach a DR=0.2670, and image [c9r] illustrates a residual image obtained using the GSRBF despeckling approach a DR=0.2767.

An ideal denoising despeckling approach restores the original image. Hence, the difference between a noise-free reference image and the corresponding ideally despeckled image should be zero. If the structure of the despeckled image is damaged by the despeckling approach in the process of removing the speckle, then the difference between a noise-free reference image and the despeckled image is greater than zero. However, the remaining speckle noise in an inefficiently despeckled image would contribute to a value greater than zero. Besides the visual assessment in FIG. 4A and FIG. 4B, the difference ratio (DR) represents the summation of pixel values of the difference image (reference noise-free image and the despeckled image) to the summation of pixel values of the reference noise-free image. The higher the DR value, the more the structure is affected. Besides the outperformance of the speckle noise suppression method of the present disclosure in terms of SNR and PSNR, and its leading performance in terms of FSIM and MSSIM, the speckle noise suppression method of the disclosure does not affect the original structure of the image in fine and rough speckle noise simulations with least DR values of 0.0787 and 0.2188, respectively, as shown in image [b3r] and image [b4r] of FIG. 4A as compared with the other despeckling approaches.

Based on Table 2 and FIG. 2A and FIG. 2B, SVD with either orthogonal or oblique projection is found to perform the same in case of either fine speckle noise or rough speckle noise experiments. This conclusion can be reached by looking at the overall average rank in the last column of Table 2. SVD is in the sixth place for either type of speckle noise. On the other hand, and in case of fine speckle noise, the Lanczos approach of the present disclosure showed a slight difference in performance between orthogonal and oblique projections, in the terms of alpha, SNR, and PSNR.

The similarity in performance of the SVD oblique projection and the SVD orthogonal projection indicates that $P_{orth.}W=P_{obli.}S$, while the negligible difference in performance between Lanczos oblique and orthogonal projection, mainly in case of the fine speckle noise experiment, indicates that $P_{orth.}W \neq P_{obli.}S$. In other words, Lanczos leaves an amount of correlation between the signal space ($V_1$) and the noise space ($V_2$) in equation (11), while the SVD does not. The unique performance of the Lanczos despeckling approach remained valid with the same despeckling parameters (r×p=8×8, k=4) for the fine speckle noise as well as for the rough speckle noise experiments. Although despeckling parameters are set the same for the Lanczos and SVD methods, the dB drop in SNR and PSNR between fine and rough noise experiments in case of the SVD is around 11 and 10, respectively, while those for the Lanczos is around 8 and 7, respectively. Overall, the Lanczos orthogonal projection of the disclosure outperformed all benchmark despeckling approach in case of the fine speckle noise experiment. The Lanczos oblique projection performed second to the Lanczos orthogonal projection. In case of the rough speckle noise experiment, the Lanczos approach with either orthogonal or oblique projection is found to perform the same and it is ranked the second after the GNLDF despeckling approach and the GSRBF despeckling approach.

Percentage wise and based on Table 2, the general performance of the Lanczos orthogonal and the Lanczos oblique methods is found to be similar for the rough speckle noise experiment. However, for the fine speckle noise experiment, the Lanczos orthogonal method has performed better than the Lanczos oblique in terms of alpha with 2.44% improvement (less alpha indicates better resolution), and in terms of PSNR with 0.036% improvement. On the other hand, the Lanczos oblique method has surpassed the Lanczos orthogonal in terms of SNR with 1.21% improvement. Due to the closeness of numerical performance between the two projection despeckling approach of the Lanczos, the orthogonal projection of Lanczos of the present disclosure is used in Table 3 as a reference to display its percentage improvement over the other existing methods.

TABLE 3

Percentage improvement of the Lanczos method over benchmark methods. Simulated images.

| Method | | Alpha (%) | CNR (%) | S-SNR (%) | SNR (%) | PSNR (%) | Beta (%) | FSIM (%) | MSSIM (%) |
|---|---|---|---|---|---|---|---|---|---|
| SVD | F | 6.25 | −10.81 | −11.20 | −18.50 | −6.08 | −6.36 | −2.59 | −5.71 |
| orth./obli. | R | 84.52 | 6.62 | −17.60 | −50.26 | −20.49 | 4.41 | −18.57 | −33.68 |
| PNLM | F | 48.75 | −5.41 | −8.56 | −6.86 | −6.02 | −19.09 | −3.67 | −5.93 |
| | R | 82.14 | 22.06 | 1.20 | −35.17 | −13.73 | −8.82 | −15.39 | −17.89 |
| Frost | F | 0 | −6.08 | −25.18 | −11.05 | −3.37 | −17.27 | −2.05 | −3.96 |
| | R | 35.71 | 8.82 | −11.29 | −29.14 | −11.21 | 4.41 | −7.29 | −17.14 |
| Lee | F | 6.25 | 0 | −27.00 | −21.23 | −8.20 | −32.72 | −5.50 | −7.36 |
| | R | 48.81 | 11.03 | −14.89 | −37.16 | −14.77 | 1.47 | −10.81 | −23.16 |
| GNLDF | F | 43.75 | −17.57 | −11.38 | −17.68 | −10.27 | −10.91 | −2.16 | −4.51 |
| | R | 71.43 | −8.088 | 0.379 | −23.84 | −10.02 | 16.18 | −7.64 | −11.58 |
| GSRBF | F | −11.25 | −29.05 | −23.68 | −14.50 | −4.42 | 4.55 | 1.29 | 0.77 |
| | R | 1.19 | −23.53 | −2.02 | −15.86 | −4.44 | 5.88 | 1.76 | 6.62 |

The percentages in Table 3 are calculated by subtracting the measurement of the benchmark despeckling approach from the corresponding measurements from the Lanczos approach and then dividing by measurement of the Lanczos approach. A negative sign in Table 3 indicates that the Lanczos despeckling approach results of the present disclosure leads the benchmark despeckling approach.

Both Tables 2 and 3 show the importance of using multiple assessment measures to correctly assess the despeckling approaches of the present disclosure. It is noticed from Table 3 that the efficiency of the method of the present disclosure is achieved at the cost of resolution. However, a higher resolution does not necessarily indicate the success of a despeckling approach. For example, the PNLM despeckling approach in Table 2 has achieved the first and the second place in terms of alpha for fine and rough speckle noise simulations, respectively. However, the PNLM despeckling approach has showed poor despeckling performance as visually can be seen in image [b5] of FIG. 2B and image [c5] of FIG. 2C. Lower alpha (better resolution) in Table 2 or higher positive percentages of alpha in Table 3 in favor of the benchmark despeckling approach are generally met by superior performance of the speckle noise suppressing method over the benchmarks in terms of the SNR, the PSNR, the beta, the FSIM, and the MSSIM. The GSRBF despeckling approach, shows a better but close performance to the methods of the present disclosure in terms of beta, the FSIM, and the MSSIM. The close performance between the Lanczos despeckling approach of the present disclosure and the GSRBF despeckling approach is apparent in the 0.77% advantage of the GSRBF despeckling approach over the Lanczos despeckling approach in terms of the MSSIM. Further, the Lanczos approach of the present disclosure shows a clear advantage over the GSRBF despeckling approach in terms CNR (F: −29.05%, R: −23.53%) and SNR (F: −14.50%, R: −15.86%) for both fine and rough speckle noise simulations. The leading performance of the methods of the present disclosure over the GSRBF despeckling approach extends to alpha (F: —11.25%) and to S-SNR (F: —23.68%) for the fine speckle noise simulation.

FIG. 5A(1) to FIG. 5I(2) show the 128th lateral (left graph) and axial (right graph) profiles of the 256×256 despeckled images of FIG. 2B and FIG. 2C for demonstrating the despeckling performances of all methods. FIG. 5A(1) illustrates a lateral profile corresponding to the SVD orthogonal subspace projection associated with a corresponding image in FIG. 2B and FIG. 2C. The lateral profile illustrates signals 502, 504 and 506. The signal 502 corresponds to the SVD orthogonal despeckling approach on the rough speckled noise image, the signal 504 corresponds to the SVD orthogonal despeckling approach on the fine speckled noise image, and the signal 508 corresponds to a noise free signal image. FIG. 5A(2) illustrates an axial profile corresponding to the SVD orthogonal subspace projection associated with a corresponding image in FIG. 2B and FIG. 2C, with signals 508, 510 and 512. The signal 508 corresponds to the SVD orthogonal despeckling approach on the rough speckled noise image, the signal 510 corresponds to the SVD orthogonal despeckling approach on the fine speckled noise image, and the signal 512 corresponds to a noise free signal.

FIG. 5B(1) illustrates a lateral profile corresponding to the SVD orthogonal subspace projection associated with a corresponding image in FIG. 2B and FIG. 2C, according to certain embodiments. The lateral profile illustrates signals 514, 516 and 518. The signal 514 corresponds to the SVD oblique despeckling approach on the rough speckled noise image, the signal 516 corresponds to the SVD oblique despeckling approach on the fine speckled noise image, and the signal 518 corresponds to a noise free signal. FIG. 5B(2) illustrates an axial profile corresponding to a SVD oblique subspace projection associated with a corresponding image, with signals 520, 522 and 524. The signal 520 corresponds to the SVD oblique despeckling approach on the rough speckled noise image, the signal 522 corresponds to the SVD oblique despeckling approach on the fine speckled noise image, and the signal 524 corresponds to a noise free signal.

FIG. 5C(1) illustrates a lateral profile corresponding to a Lanczos orthogonal subspace projection associated with a corresponding image in FIG. 2B and FIG. 2C. The lateral profile illustrates signals 526, 528 and 530. The signal 526 corresponds to the Lancz orthogonal despeckling approach on the rough speckled noise image, the signal 528 corresponds to the Lancz orthogonal despeckling approach on the fine speckled noise image, and the signal 530 corresponds to a noise free signal. FIG. 5C(2) illustrates an axial profile corresponding to the Lanczos orthogonal subspace projection associated with a corresponding image in FIG. 2B and FIG. 2C, with signals 532, 534 and 536. The signal 532 corresponds to the Lancz oblique despeckling approach on the rough speckled noise image, the signal 534 corresponds to the Lancz despeckling approach on the fine speckled noise image, and the signal 536 corresponds to a noise free signal.

FIG. 5D(1) illustrates a lateral profile corresponding to a Lanczos oblique subspace projection associated with a corresponding image in FIG. 2B and FIG. 2C. The lateral profile illustrates signals 538, 540 and 542. The signal 538 corresponds to the Lancz oblique despeckling approach on the rough speckled noise image, the signal 540 corresponds to the Lancz oblique despeckling approach on the fine speckled noise image, and the signal 542 corresponds to a noise free signal. FIG. 5D(2) illustrates an axial profile corresponding to the Lanczos oblique subspace projection associated with a corresponding image in FIG. 2B and FIG. 2C, with signals 544, 546 and 548. The signal 544 corresponds to the Lancz oblique despeckling approach on the rough speckled noise image, the signal 546 corresponds to the Lancz oblique despeckling approach on the fine speckled noise image, and the signal 548 corresponds to a noise free signal.

FIG. 5E(1) illustrates a lateral profile corresponding to the PNLM subspace projection associated with a corresponding image in FIG. 2B and FIG. 2C. The lateral profile illustrates signals 550, 552 and 554. The signal 550 corresponds to the PNLM despeckling approach on the rough speckled noise image, the signal 552 corresponds to the PNLM despeckling approach on the fine speckled noise image, and the signal 554 corresponds to a noise free signal. FIG. 5E(2) illustrates an axial profile corresponding to the PNLM subspace projection associated with a corresponding image in FIG. 2B and FIG. 2C, with signals 556, 558 and 560. The signal 556 corresponds to the PNLM despeckling approach on the rough speckled noise image, the signal 558 corresponds to the PNLM despeckling approach on the fine speckled noise image, and the signal 560 corresponds to a noise free signal.

FIG. 5F(1) illustrates a lateral profile corresponding to a Frost subspace projection associated with a corresponding image in FIG. 2B and FIG. 2C. The lateral profile illustrates signals 562, 564 and 566. The signal 562 corresponds to the Frost despeckling approach on the rough speckled noise image, the signal 564 corresponds to the Frost despeckling approach on the fine speckled noise image, and the signal 566 corresponds to a noise free signal. FIG. 5F(2) illustrates an axial profile corresponding to the Frost subspace projection associated with a corresponding image in FIG. 2B and FIG. 2C, with signals 568, 570 and 572. The signal 568 corresponds to the Frost despeckling approach on the rough speckled noise image, the signal 570 corresponds to the Frost despeckling approach on the fine speckled noise image, and the signal 572 corresponds to a noise free signal.

FIG. 5G(1) illustrates a lateral profile corresponding to a Lee subspace projection associated with a corresponding image in FIG. 2B and FIG. 2C. The lateral profile illustrates signals 574, 576 and 578. The signal 574 corresponds to the Lee despeckling approach on the rough speckled noise image, the signal 576 corresponds to the Lee despeckling approach on the fine speckled noise, and the signal 578 corresponds to a noise free signal. FIG. 5G(2) illustrates an axial profile corresponding to the Lee subspace projection associated with a corresponding image in FIG. 2B and FIG. 2C, with signals 580, 582 and 584. The signal 580 corresponds to the Lee despeckling approach on the rough speckled noise the, the signal 582 corresponds to the Lee despeckling approach on the fine speckled noise image, and the signal 584 corresponds to a noise free signal.

FIG. 5H(1) illustrates a lateral profile corresponding to a GNLDF subspace projection associated with a corresponding image in FIG. 2B and FIG. 2C. The lateral profile illustrates signals 586, 588 and 590. The signal 586 corresponds to the GNLDF despeckling approach on the rough speckled noise image, the signal 588 corresponds to the GNLDF despeckling approach on the fine speckled noise image, and the signal 590 corresponds to a noise free signal. FIG. 5H(2) illustrates an axial profile corresponding to the GNLDF subspace projection associated with a corresponding image in FIG. 2B and FIG. 2C, with signals 592, 594 and 596. The signal 592 corresponds to the GNLDF despeckling approach on the rough speckled noise image, the signal 594 corresponds to the GNLDF despeckling approach on the fine speckled noise image, and the signal 596 corresponds to a noise free signal.

FIG. 5I(1) illustrates a lateral profile corresponding to a GSRBF subspace projection associated with a corresponding image in FIG. 2B and FIG. 2C. The lateral profile illustrates signals 598, 600 and 602. The signal 598 corresponds to the SVD orthogonal despeckling approach on the rough speckled noise image, the signal 600 corresponds to the SVD orthogonal despeckling approach on the fine speckled noise image, and the signal 602 corresponds to a noise free signal. FIG. 5I(2) illustrates an axial profile corresponding to the GSRBF subspace projection associated with a corresponding image in FIG. 2B and FIG. 2C, with signals 604, 606 and 608. The signal 604 corresponds to the SVD oblique despeckling approach on the rough speckled noise image, the signal 606 corresponds to the SVD oblique despeckling approach on the fine speckled noise image, and the signal 608 corresponds to a noise free signal.

The Lanczos despeckling approach with either orthogonal or oblique projections results in the closest profiles to the noise-free images compared to all other benchmark despeckling approach. The profiles of the GNLDF despeckling approach in FIG. 5H(1) and FIG. 5H(2) both differ from the noise-free profiles compared to the Lanczos approach of the present disclosure, and the axial profiles are also corrupted with spikes especially around edges. Such spikes also corrupt the axial profiles of the PNLM despeckling approach, and of the Frost despeckling approach and the Lee despeckling approach. The GSRBF despeckling approach, in the case of fine speckle noise shows a good approximation to the noise-free profiles, but when compared with the Lanczos approach of the present disclosure for the case of rough speckle noise, the GSRBF despeckling approach fails to show a good approximation as can be seen in FIG. 5I(1) and FIG. 5I(2) when compared with FIG. 5C(1), FIG. 5C(2) and FIG. 5D(1) and FIG. 5D(2).

Figure 6:
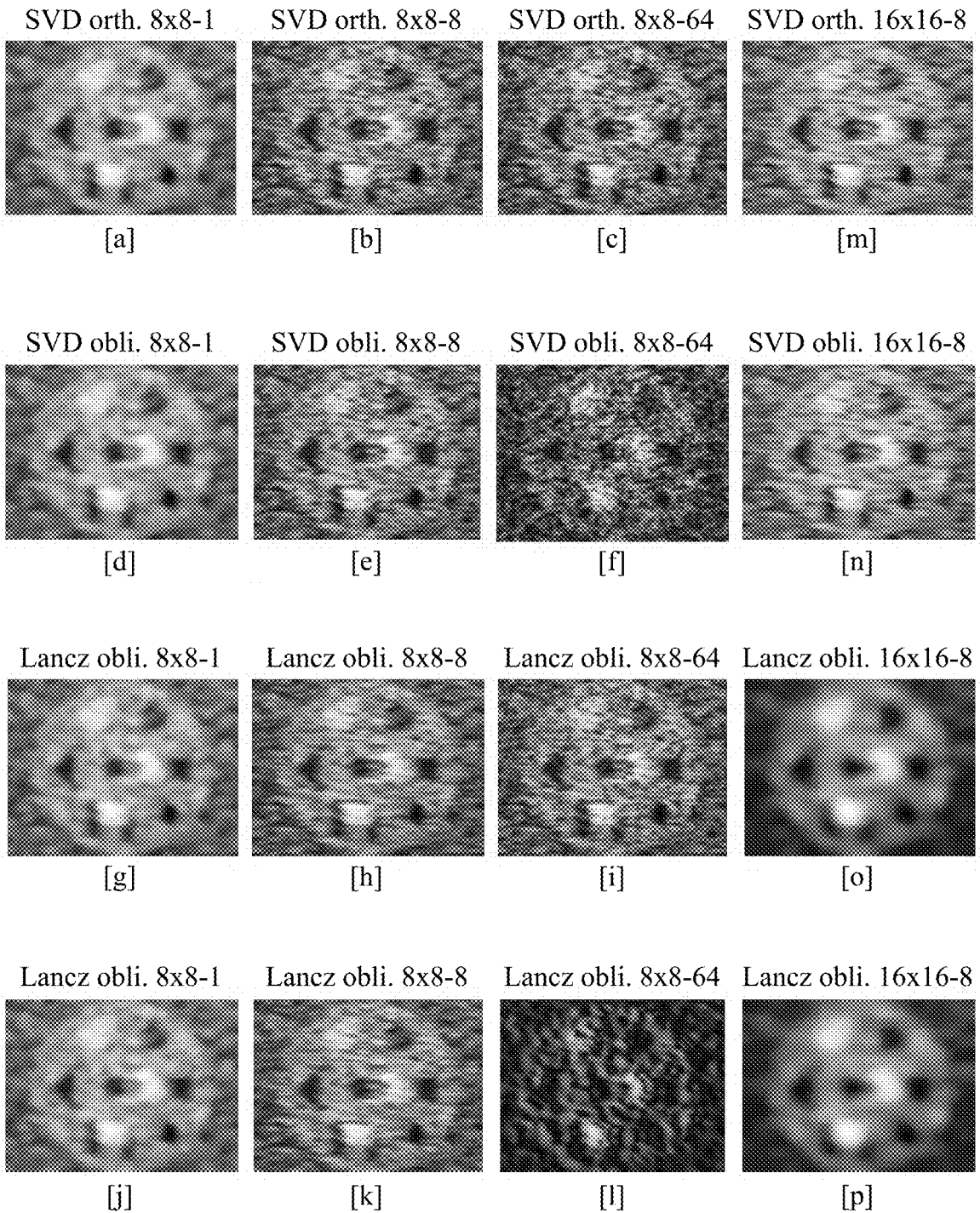
FIG. 6 illustrates a visual performance of an SVD despeckling approach and a Lanczos despeckling approach with different orthonormal vectors and block size, according to certain embodiments.

FIG. 6 shows the performance of the SVD despeckling approach and the Lanczos despeckling approach with different number of orthonormal vectors and block sizes (r×p, k) for images illustrated in FIG. 2A. Image [a] of FIG. 6 illustrates the performance of the SVD despeckling approach with orthonormal vectors and block sizes (8×8, 1). Image [b] of FIG. 6 illustrates the performance of the SVD despeckling approach with orthonormal vectors and block sizes (8×8, 8). Image [c] of FIG. 6 illustrates the performance of the SVD despeckling approach with orthonormal vectors and block sizes (8×8, 64). Image [d] of FIG. 6 illustrates the performance of the SVD despeckling approach with orthonormal vectors and block sizes (8×8, 1). Image [e] of FIG. 6 illustrates the performance of the SVD despeckling approach with orthonormal vectors and block sizes (8×8, 8). Image [f] of FIG. 6 illustrates the performance of the SVD despeckling approach with orthonormal vectors and block sizes (8×8, 64). Image [g] of FIG. 6 illustrates the performance of the Lanczos oblique despeckling approach with orthonormal vectors and block sizes (8×8, 1). Image [h] of FIG. 6 illustrates the performance of the Lanczos oblique despeckling approach with orthonormal vectors and block sizes (8×8, 8). Image [i] of FIG. 6 illustrates the performance of the Lanczos oblique despeckling approach with orthonormal vectors and block sizes (8×8, 64). Image [j] of FIG. 6 illustrates the performance of the Lanczos oblique despeckling approach with orthonormal vectors and block sizes (8×8, 1). Image [k] of FIG. 6 illustrates the performance of the Lanczos oblique despeckling approach with orthonormal vectors and block sizes (8×8, 8). Image [1] of FIG. 6 illustrates the performance of the Lanczos oblique with orthonormal vectors and block sizes (8×8, 64). Image [m] of FIG. 6 illustrates the performance of the SVD orthogonal approach with orthonormal vectors and block sizes (16×16, 8). Image [n] of FIG. 6 illustrates the performance of the SVD oblique despeckling approach with orthonormal vectors and block sizes (16×16, 8). Image [o] of FIG. 6 illustrates the performance of the Lanczos oblique despeckling approach with orthonormal vectors and block sizes (16×16, 8). Image [p] of FIG. 6 illustrates the performance of the Lanczos oblique despeckling approach with orthonormal vectors and block sizes (16×16, 8).

A block size of 8×8 with one orthonormal vector will cause the SVD and the Lanczos to perform the same with considerable blur as shown in image [a], image [d], image [g] and image [j] of FIG. 6. A block size of 8×8 with eight orthonormal vectors provides an advantage to the Lanczos approach over the SVD approach. However, the images remain inefficiently despeckled as shown in image [b], image [e], image [h] and image [k]. Any block size with all orthonormal vectors, i.e., 64 orthonormal vectors in case of 8×8 block size, leaves the image undespeckled if subjected to orthogonal projection as shown in image [c] and image [i] of FIG. 6. If an image is subjected to oblique projection with all orthonormal vectors, the speckle noise would appear decorrelated in case of the SVD approach as shown in image [f] of FIG. 6, and correlated with some distortion in case of the Lanczos approach as shown image [I] of FIG. 6. The reason for this correlation/decorrelation or distortion is the full overlap, when all orthonormal vectors are used, between signal space and noise space in equation (11) and the difference in efficiency between the Lanczos and the SVD approaches in estimating the orthonormal vectors.

The difference in performance between the SVD approach and the Lanczos approach is seen if a block size of 16×16 with eight orthonormal vectors is used as shown in image [m], image [n], image [o] and image [p] of FIG. 6, where orthogonal and oblique projections are equivalent for each decomposition despeckling approach. The image looks inefficiently despeckled in case of the SVD approach as shown in image [m] and image [n], and oversmoothed in case of the Lanczos approach of the present disclosure as shown in image [o] and image [p].

Real images for kidney, liver and lymph node are processed and the values are tabulated in Table 4. Among the aforementioned images, the appearance of speckle noise varies between fine and rough. The Lanczos approach of the disclosure along with SVD and the other benchmark despeckling approaches are applied with the despeckling parameters listed in Table 1. Parameters are tuned and adjusted to yield best despeckling results and to avoid blur. Table 4 lists the numerical performance that corresponds to the visual performance of despeckling approaches shown in FIG. 7 to FIG. 8. Due to the absence of the noise-free reference image, the assessing measures of Alpha, CNR, and S-SNR were used.

TABLE 4

Numerical performance of despeckling approaches when applied to real medical ultrasound images.

| Method | Kidney | | | Liver | | | Lymph | | |
| --- | --- | --- | --- | --- | --- | --- | --- | --- | --- |
| | Alpha | CNR | S-SNR | Alpha | CNR | S-SNR | Alpha | CNR | S-SNR |
| Noisy img. | 0.027 | 0.429 | 2.754 | 0.053 | 0.245 | 1.902 | 0.040 | 0.344 | 1.487 |
| SVD orth. | 0.078(3) | 0.366(3) | 2.865(5) | 0.075(3) | 0.203(4) | 1.930(6) | 0.059(2) | 0.297(2) | 1.528(7) |
| SVD obli. | 0.078(3) | 0.366(3) | 2.865(5) | 0.075(3) | 0.203(4) | 1.930(6) | 0.059(2) | 0.297(2) | 1.528(7) |
| Lanczos orth. | 0.098(7) | 0.314(5) | 3.067(1) | 0.082(5) | 0.204(3) | 2.017(3) | 0.083(7) | 0.260(6) | 1.716(1) |
| Lanczos obli. | 0.098(7) | 0.314(5) | 3.067(1) | 0.082(5) | 0.204(3) | 2.017(3) | 0.083(7) | 0.260(6) | 1.716(1) |
| PNLM | 0.036(1) | 0.457(1) | 2.824(6) | 0.056(1) | 0.297(1) | 2.013(4) | 0.030(1) | 0.278(5) | 1.622(4) |
| Frost | 0.091(5) | 0.345(4) | 2.941(4) | 0.081(4) | 0.200(5) | 1.977(5) | 0.070(5) | 0.288(4) | 1.602(5) |
| Lee | 0.073(2) | 0.399(2) | 2.811(7) | 0.083(6) | 0.229(2) | 1.926(7) | 0.067(3) | 0.324(1) | 1.554(6) |
| GNLDF | 0.082(4) | 0.250(7) | 2.980(3) | 0.072(2) | 0.165(7) | 2.025(2) | 0.068(4) | 0.289(3) | 1.669(3) |
| GSRBF | 0.097(6) | 0.286(6) | 3.029(2) | 0.082(5) | 0.179(6) | 2.027(1) | 0.080(6) | 0.217(7) | 1.675(2) |

By comparing alpha, CNR, and S-SNR in Table 4 with those in Table 2, it can be noticed that the ranks of the despeckling approaches in both tables parallel one another. In Table 2, the Lanczos approach of the present disclosure showed a relatively lagging performance in terms of alpha, which was always outshone by a leading performance in terms of key assessing measures such as SNR, PSNR, FSIM, and MSSIM. The same observation is supported by Table 5 when compared with Table 3. Table 5 is created similar to Table 3. Table 5 is provided below.

TABLE 5

Percentage improvement of the Lanczos despeckling approach of the disclosure over benchmark methods. Real images.

| Method | Kidney | | | Liver | | | Lymph | | |
|---|---|---|---|---|---|---|---|---|---|
| | Alpha | CNR | S-SNR | Alpha | CNR | S-SNR | Alpha | CNR | S-SNR |
| SVD orth./obli. | 20.41 | 16.56 | −6.59 | 8.54 | −0.49 | −4.31 | 28.92 | 14.23 | −10.96 |
| PNLM | 63.27 | 45.54 | −7.923 | 31.71 | 45.59 | −0.20 | 63.86 | 6.92 | −5.48 |
| Frost | 7.14 | 9.87 | −4.11 | 1.22 | −1.96 | −1.98 | 15.66 | 10.77 | −6.64 |
| Lee | 25.51 | 27.07 | −8.35 | −1.22 | 12.25 | −4.51 | 19.28 | 24.62 | −9.44 |
| GNLDF | 16.33 | −20.38 | −2.84 | 12.20 | −19.12 | 0.40 | 18.07 | 11.15 | −2.74 |
| GSRBF | 1.02 | −8.92 | −1.24 | 0 | −12.25 | 0.50 | 3.61 | −16.54 | −2.39 |

The resolution parameter alpha that shows the advantage of benchmark despeckling approach over the Lanczos despeckling approach of the present disclosure, and the parameter CNR that shows a slight advantage of the methods of the present disclosure over benchmark despeckling approaches are indications of the higher performance of the methods of the present disclosure over benchmark despeckling approaches in terms of the SNR, the PSNR, the FSIM, and the MSSIM. This observation leads to a conclusion that the Lanczos approach of the present disclosure provides maximum numerical performance in terms of the SNR, the PSNR, the FSIM, and the MSSIM for the real ultrasound images. The beta parameter tends to show sensitivity to the nature of the speckle noise (fine or rough) and the stability of the methods of the present disclosure in overcoming the spikes mainly around the edges of the image. The same conclusion is obtained by investigating the despeckled images in FIG. 7, where the Lanczos approach of the present disclosure provided maximum cleaning of speckle noise as shown in image [a3] and image [a4] of FIG. 7, image [b3] and image [b4] of FIG. 8, image [c3] and image [c4] of FIG. 9. Based on the numerical results in Table 4, Table 5, and on the visual results in FIG. 7, the GNLDF despeckling approach, the PNLM despeckling approach, the Frost despeckling approach, the Lee despeckling approach, and the GSRBF despeckling approach measurements show a similar performance in comparison to their performance in the simulated experiment. The GSRBF despeckling approach measurement is numerically expected to perform the same as in the simulated experiment and that is to provide relatively leading but close performance to the method of the present disclosure in terms of the beta, the FSIM, and the MSSIM measurements. This expectation is also based on the visual assessment for the image [a9], image [b9] and image [c9] of FIG. 7. The PNLM despeckling approach performance is usually accompanied by artifacts especially at the sides or around the edges of simulated and real images. The artifacts are visible around the edges in the simulated rough noise experiment in image [c5] of FIG. 2, as well as in the real experiment in image [a5] of FIG. 7, image [b5] of FIG. 8 and image [c5] of FIG. 9.

Figure 7:
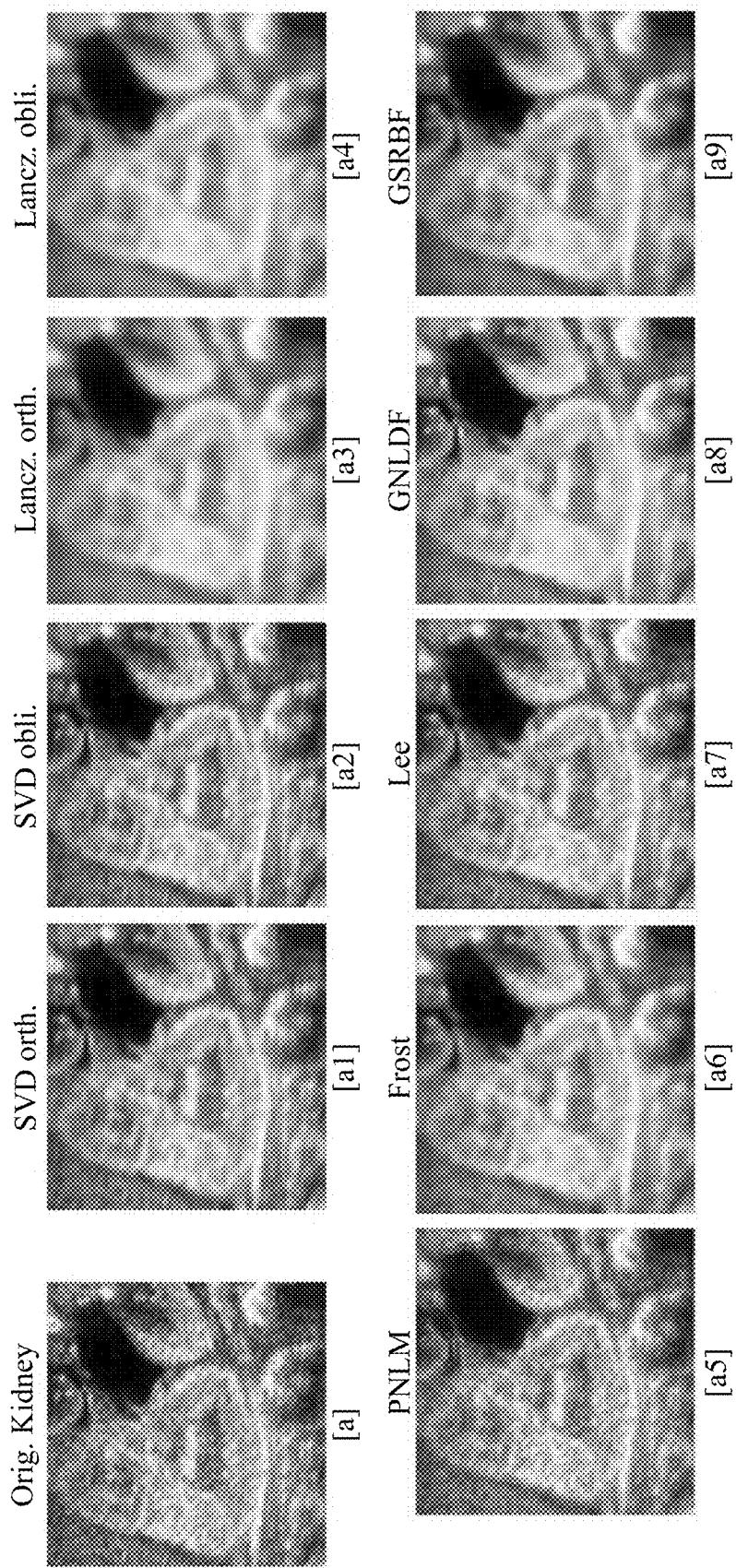
FIG. 7 illustrates a visual performance of despeckling approaches on real ultrasound image of a kidney, according to certain embodiments.

FIG. 7 illustrates a visual performance of despeckling approaches on a real ultrasound image of a kidney, according to certain embodiments. FIG. 7 illustrates an original image [a] of the kidney, an image [a1] illustrating a visual performance of SVD orthogonal despeckling approach on the original image [a], an image [a2] illustrating a visual performance of the SVD oblique despeckling approach on the original image [a], an image [a3] illustrating a visual performance of Lanczos orthogonal despeckling approach on the original image [a], an image [a4] illustrating a visual performance of the Lanczos oblique despeckling approach on the original image [a], an image [a5] illustrating a visual performance of the PNLM despeckling approach on the original image [a], an image [a6] illustrating a visual performance of the Frost despeckling approach on the original image [a], an image [a7] illustrating a visual performance of the Lee despeckling approach on the original image [a], an image [a8] illustrating visual performance of the GNLDF despeckling approach on the original image [a], and an image [a9] illustrating visual performance of the GSRBF despeckling approach on the original image [a].

Figure 8:
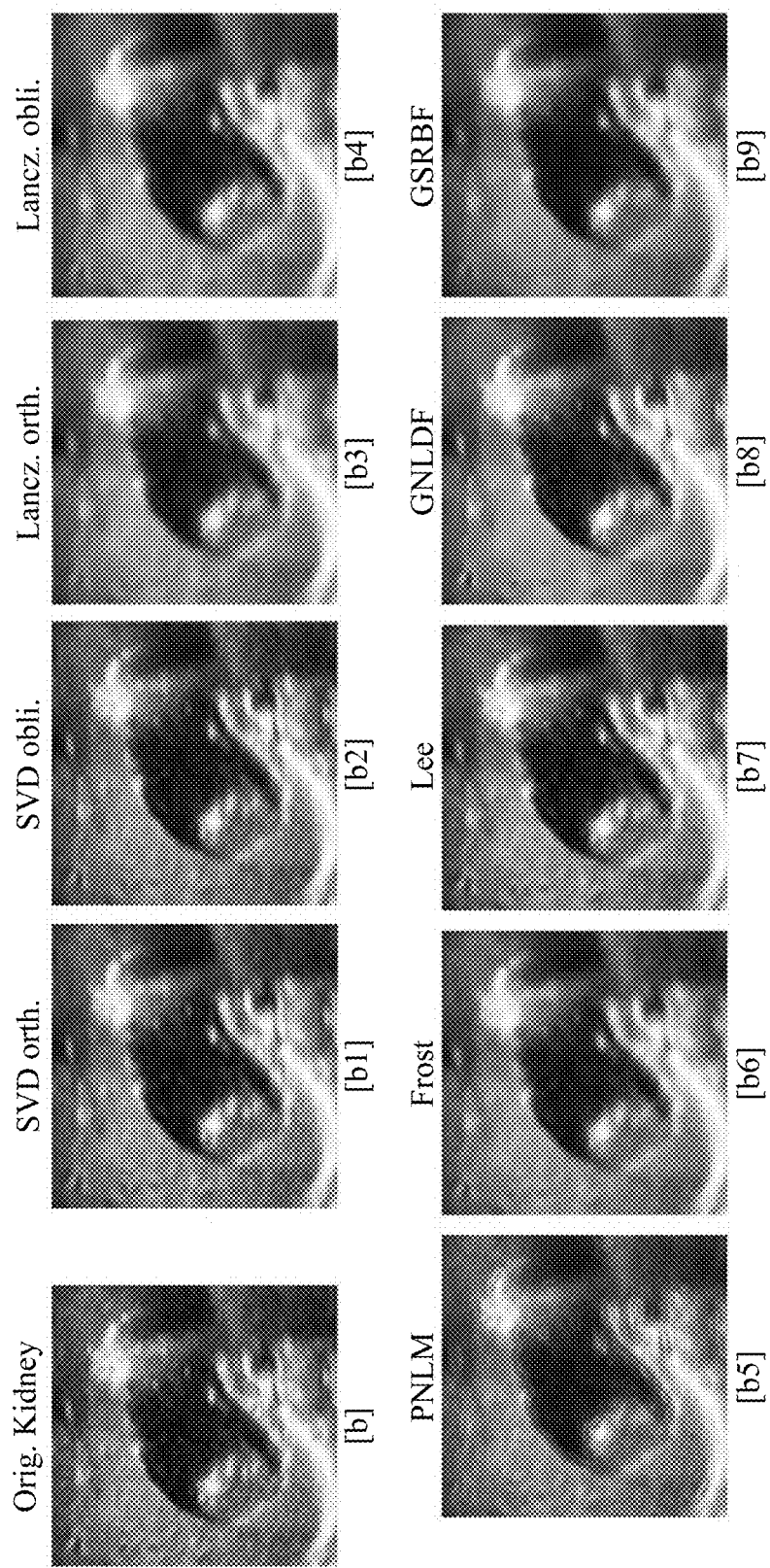
FIG. 8 illustrates a visual performance of despeckling approaches on real ultrasound image of a liver, according to certain embodiments.

FIG. 8 illustrates a visual performance of despeckling approaches on a real ultrasound image of a liver, according to certain embodiments. FIG. 8 illustrates an original image [b] of the liver, an image [b1] illustrating a visual performance of the SVD orthogonal despeckling approach on the original image [b], an image [b2] illustrating a visual performance of the SVD oblique despeckling approach on the original image [b], an image [b3] illustrating a visual performance of Lancz orthogonal despeckling approach on the original image [b], an image [b4] illustrating a visual performance of Lanczos oblique despeckling approach on the original image [b], an image [b5] illustrating a visual performance of PNLM despeckling approach on the original image [b], an image [b6] illustrating a visual performance of the Frost despeckling approach on the original image [b], an image [b7] illustrating a visual performance of the Lee despeckling approach on the original image [b], an image [b8] illustrating a visual performance of the GNLDF despeckling approach on the original image [b], and an image [b9] illustrating a visual performance of the GSRBF despeckling approach on the original image [b].

Figure 9:
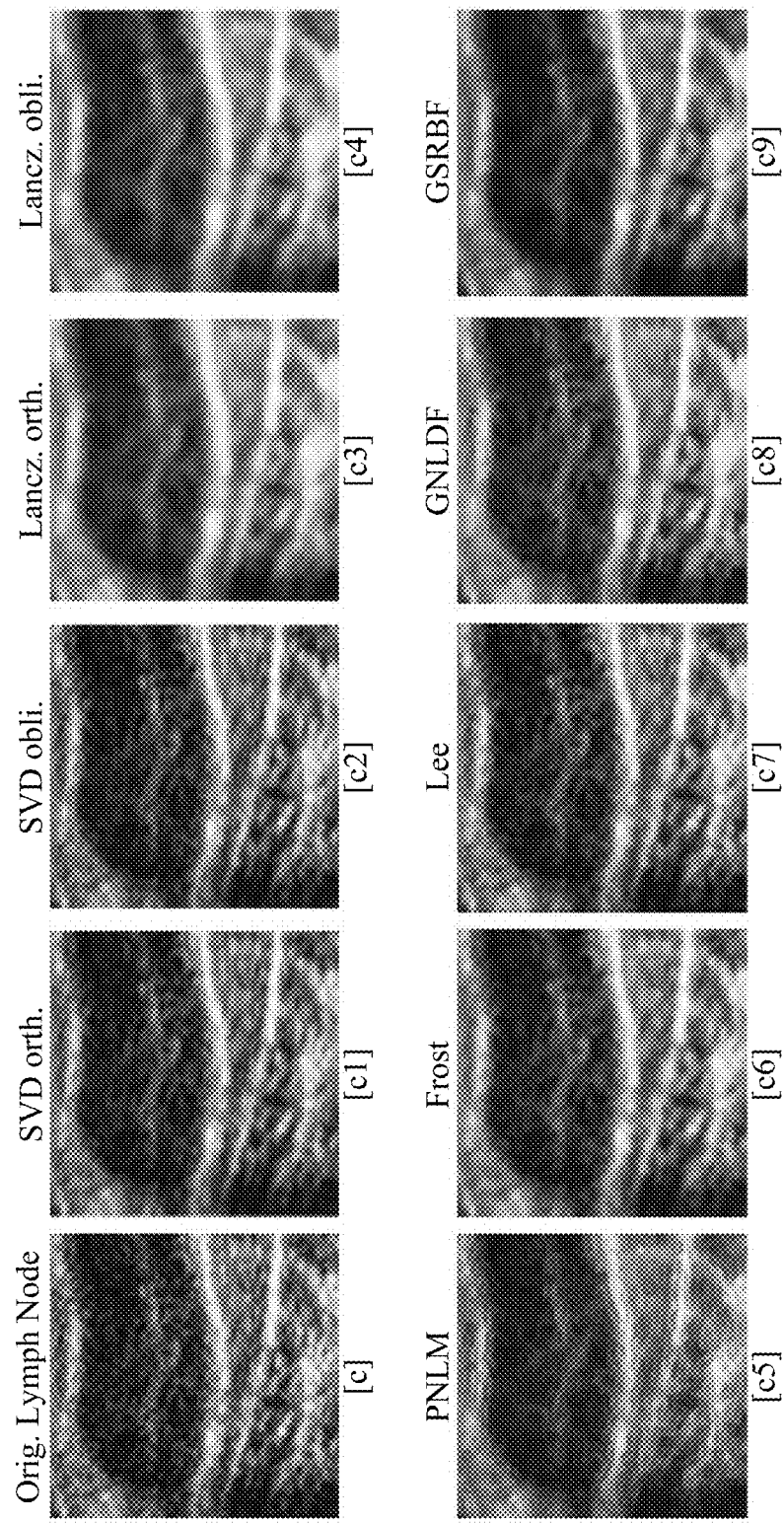
FIG. 9 illustrates a visual performance of despeckling approaches on real ultrasound image of a lymph node, according to certain embodiments.

FIG. 9 illustrates a visual performance of despeckling approaches on a real ultrasound image of a lymph node, according to certain embodiments. FIG. 8 illustrates an original image [c] of the liver, an image [c1] illustrating a visual performance of SVD orthogonal despeckling approach on the original image [c], an image [c2] illustrating a visual performance of the SVD oblique despeckling approach on the original image [c], an image [c3] illustrating a visual performance of Lancz orthogonal despeckling approach on the original image [c], an image [c4] illustrating a visual performance of Lanczos oblique despeckling approach on the original image [c], an image [c5] illustrating a visual performance of the PNLM despeckling approach on the original image [c], an image [c6] illustrating a visual performance of the Frost despeckling approach on the original image [c], an image [c7] illustrating a visual performance of the Lee despeckling approach on the original image [c], an image [c8] illustrating visual performance of the GNLDF despeckling approach on the original image [c], and an image [c9] illustrating visual performance of the GSRBF despeckling approach on the original image [c]. The efficiency of despeckling approaches is also assessed through the residual images shown in FIG. 10 to FIG. 12 for the kidney, liver, and lymph node, respectively.

Figure 10:
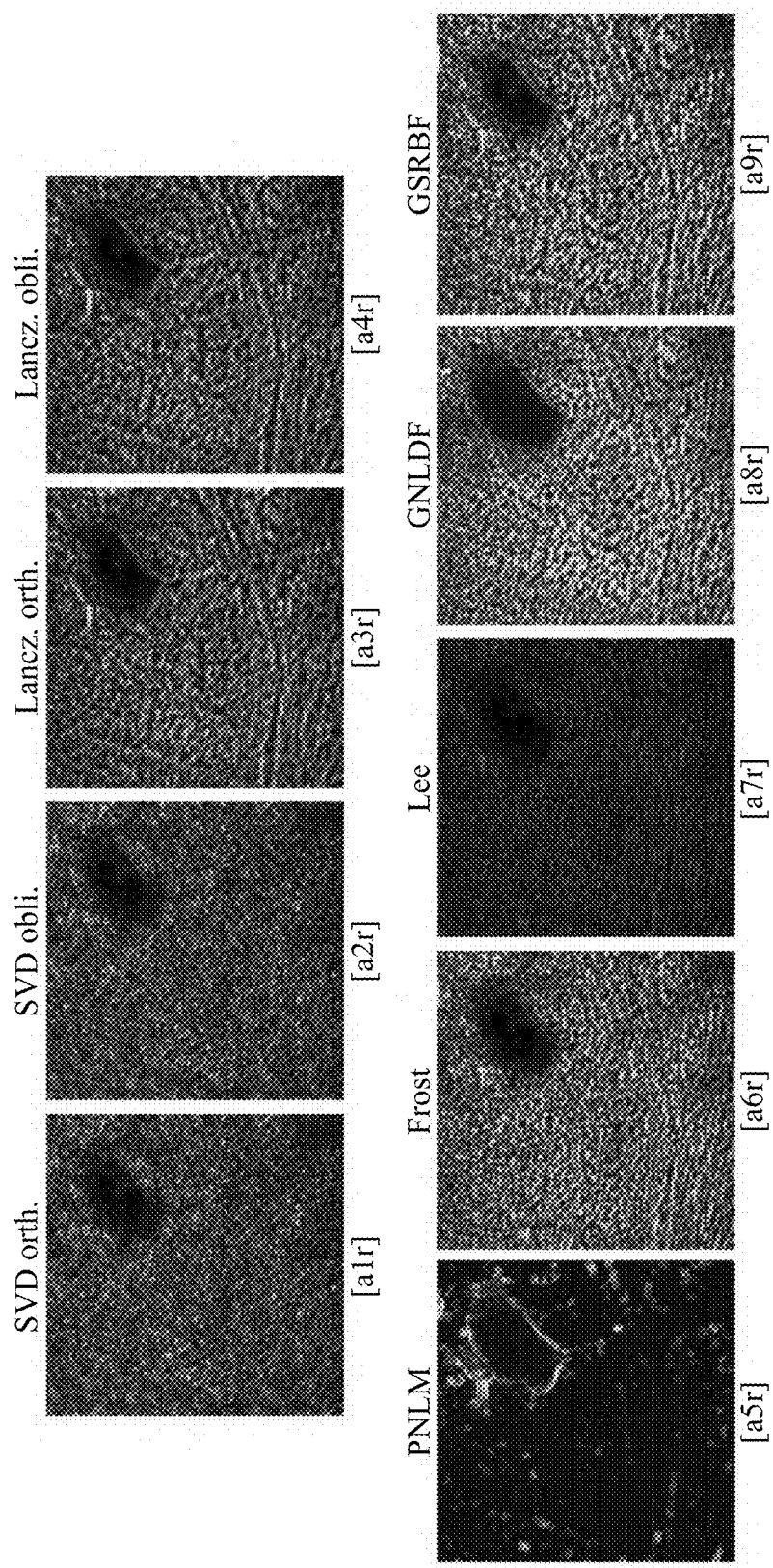
FIG. 10 illustrates a residual kidney images of despeckling approaches as a difference between speckle noise image corresponding to FIG. 7 and a despeckled image, according to certain embodiments.

FIG. 10 illustrates a residual kidney images of despeckling approaches as a difference between speckle noisy image corresponding to FIG. 7 and a despeckled image, according to certain embodiments. FIG. 10 includes an image [a1r] that illustrates a residual kidney image of SVD orthogonal despeckling approach, an image [a2r] illustrating a residual kidney image of the SVD oblique despeckling approach, an image [a3r] illustrating a residual kidney image of Lancz orthogonal despeckling approach, an image [a4r] illustrating a residual kidney image of Lanczos oblique despeckling approach, an image [a5r] illustrating a residual kidney image of PNLM despeckling approach, an image [a6r] illustrating a residual kidney image of the Frost despeckling approach, an image [a7r] illustrating a residual kidney image of the Lee despeckling approach, an image [a8r] illustrating a residual kidney image of the GNLDF despeckling approach, and an image [a9r] illustrating a residual kidney image of the GSRBF despeckling approach.

Figure 11:
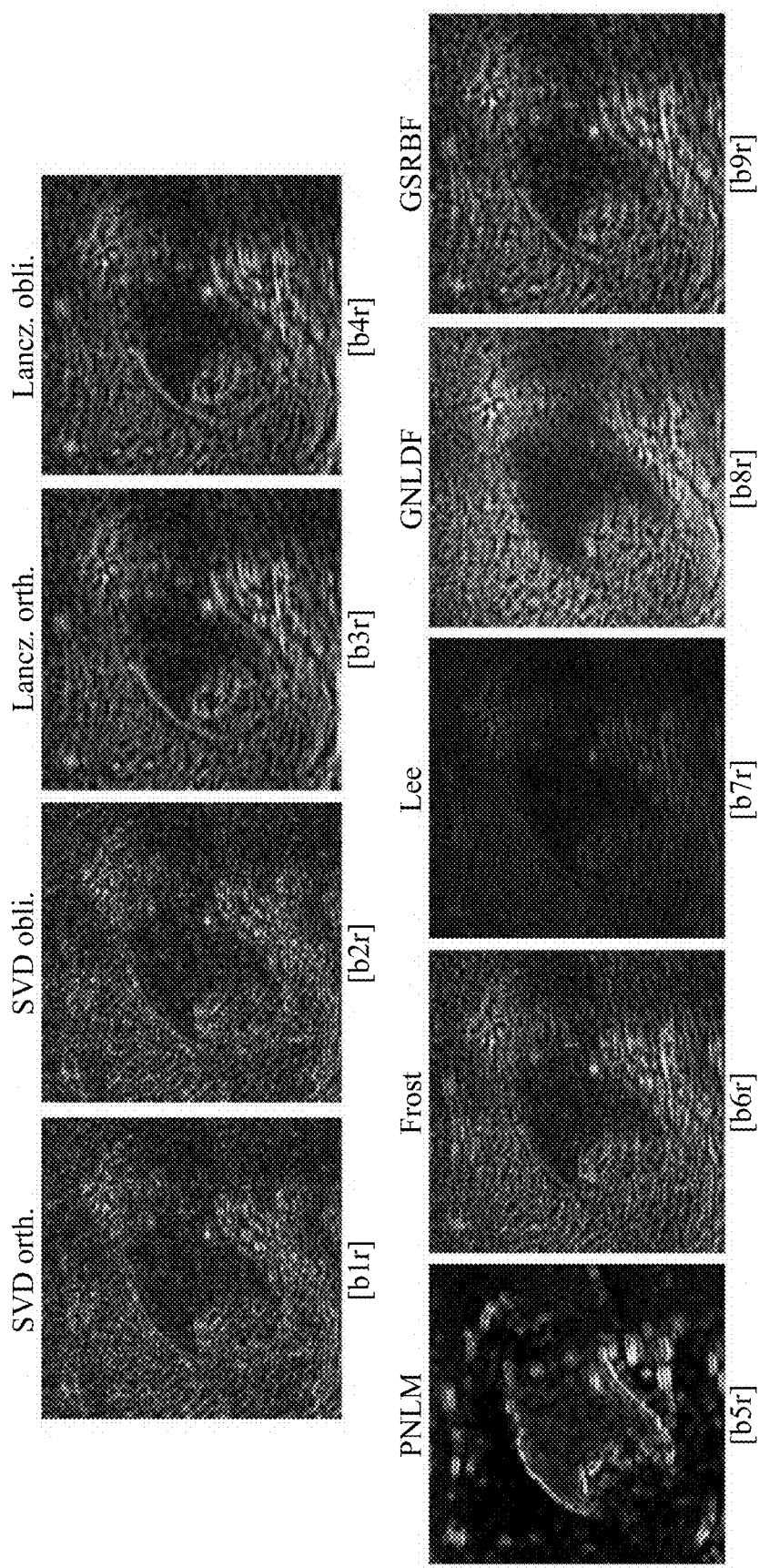
FIG. 11 illustrates a residual liver images of despeckling approaches as a difference between speckle noise image corresponding to FIG. 8 and a despeckled image, according to certain embodiments.

FIG. 11 illustrates a residual liver images of despeckling approaches as a difference between speckle noisy image corresponding to FIG. 8 and a despeckled image, according to certain embodiments. FIG. 11 includes an image [b1r] that illustrates a residual liver image of the SVD orthogonal despeckling approach, an image [b2r] illustrating a residual liver image of the SVD oblique despeckling approach, an image [b3r] illustrating a residual liver image of Lancz orthogonal despeckling approach, an image [b4r] illustrating a residual liver image of Lanczos oblique despeckling approach, an image [b5r] illustrating a residual liver image of PNLM despeckling approach, an image [b6r] illustrating a residual liver image of the Frost despeckling approach, an image [b7r] illustrating a residual liver image of the Lee despeckling approach, an image [b8r] illustrating a residual liver image of the GNLDF despeckling approach, and an image [b9r] illustrating a residual liver image of the GSRBF despeckling approach.

Figure 12:
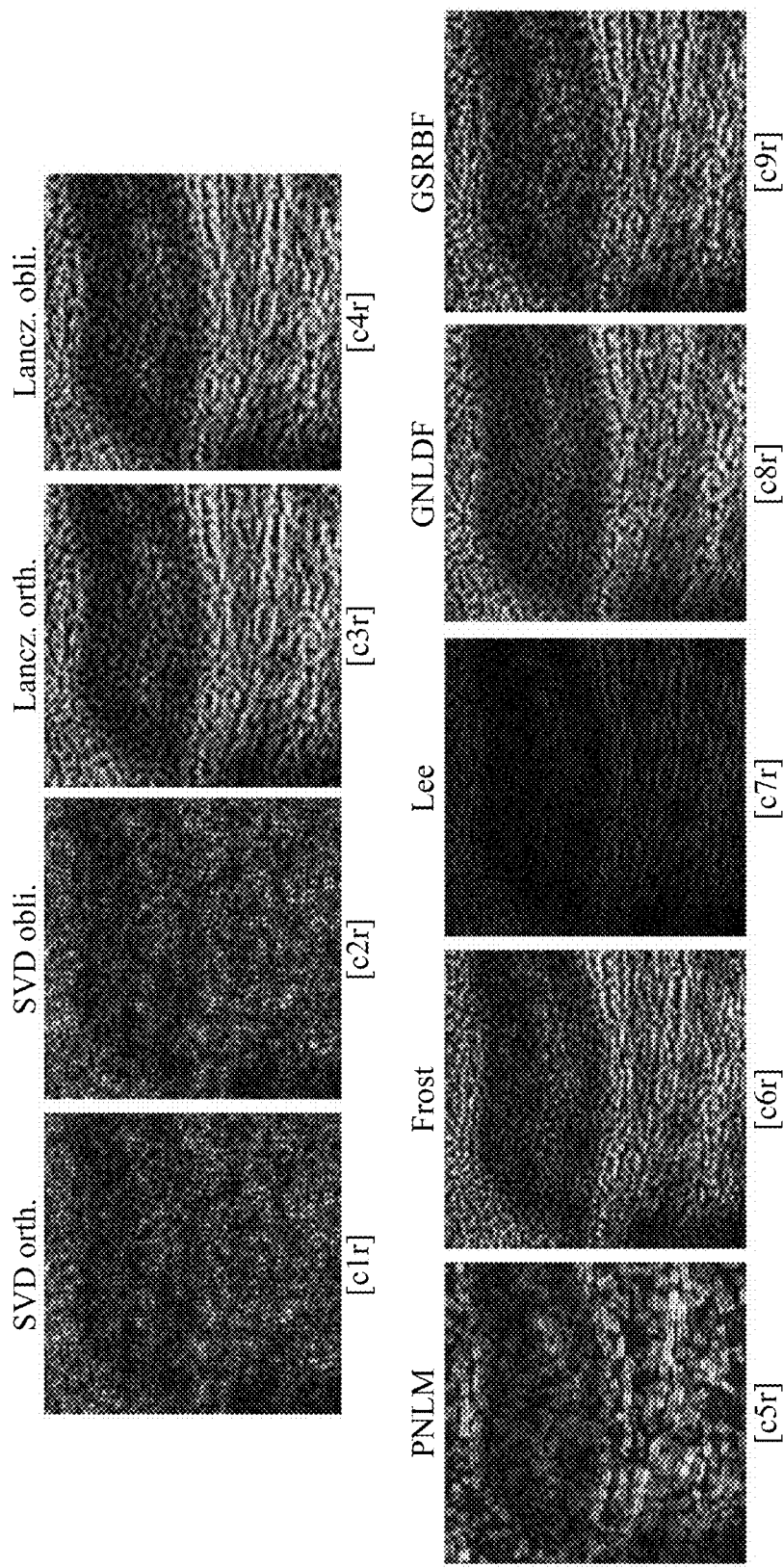
FIG. 12 illustrates a residual lymph images of despeckling approaches as a difference between speckle noise image corresponding to FIG. 9 and a despeckled image, according to certain embodiments.

FIG. 12 illustrates a residual lymph images of despeckling approaches as a difference between speckle noisy image corresponding to FIG. 9 and a despeckled image, according to certain embodiments. FIG. 12 includes an image [c1r] illustrating a residual lymph image of SVD orthogonal despeckling approach, an image [c2r] illustrating a residual lymph image of the SVD oblique despeckling approach, an image [c3r] illustrating a residual lymph image of Lancz orthogonal despeckling approach, an image [c4r] illustrating a residual lymph image of Lanczos oblique despeckling approach, an image [c5r] illustrating a residual lymph image of PNLM despeckling approach, an image [c6r] illustrating a residual lymph image of the Frost despeckling approach, an image [c7r] illustrating a residual lymph image of the Lee despeckling approach, an image [c8r] illustrating a residual lymph image of the GNLDF despeckling approach, and an image [c9r] illustrating visual performance of the GSRBF despeckling approach.

In parallel with the findings in the simulated experiment, the Lanczos of the disclosure is found leading the benchmark despeckling approach in removing the speckle noisy layer obstructing the structures as seen in image [a1r] of FIG. 10, image [b1r] of FIG. 11 and image [c1r] of FIG. 10. The GNLDF despeckling approach and the GSRBF despeckling approach show a relatively good performance in removing speckle noise as shown in FIG. 10 to FIG. 12. In FIG. 10 to FIG. 12, the Frost despeckling approach shows a better performance than the Lee despeckling approach in removing speckle noise. The PNLM despeckling approach is found to be highly affected by the geometrical shapes. Particularly, the PNLM despeckling approach is found affected by sharp edges and it does not remove speckle noise from flat patches and from around the edges with the same degree. Based on observation in image [c5r] of FIG. 12, when compared to image [a5r] of FIG. 10 or image [b5r] of FIG. 11. The SVD has showed a similar performance to what it showed in the residual images of FIG. 3A and FIG. 3B of the simulated experiment. By investigating the residual images of FIG. 10 to FIG. 12 for the SVD and by comparing them with the Lanczos despeckling approach, the GNLDF despeckling approach, the GSRBF despeckling approach, or even the Frost despeckling approach it is apparent that the SVD despeckling approach is able to remove fine speckle noise existing among rough speckle noise clusters, leaving the rough speckle noise clusters despeckled inefficiently.

The computational complexity varies between the approaches. For N pixels in the image, the Frost despeckling approach and the Lee despeckling approaches have a similar complexity of $O(N^2K)$, where K is the number of iterations. For a window size "h," the PNLM despeckling approach has a complexity of $O(N^2h^2)$. The GNLDF despeckling approach has a complexity of $O(N)$. The GSRBF despeckling approach consists of two stages: the GF with a complexity of $O(N)$ and the SRBF with a complexity of $O(Nh^2)$, where "h" is the window size. Hence, the overall complexity of the GSRBF despeckling approach is $O(Nh^2)$. The complexity of the approach of the present disclosure using the SVD is dominated by the $O(N^3)$ complexity of SVD algorithm. The complexity of the approach of the present disclosure using Lanczos is dominated by $O(N^2)$ the complexity of Lanczos algorithm. The eigen-based decomposition scheme such as QR has similar complexity as the SVD despeckling approach, however, the SVD despeckling approach is chosen against the Lanczos despeckling approach due to its numerical stability. If the image is despeckled axially and then laterally, the size of the covariance matrix would be r·pxr·p instead of r·pxr·p in equation (9). This would decrease the complexity by a power of half to result in $O(N^{3/2})$ for the SVD and $O(N)$ for the Lanczos despeckling approach. Besides the despeckling efficiency of the Lanczos approach, it also shows a competitive computational complexity when compared with those of benchmark despeckling approach.

The benchmark despeckling approaches, i.e., the PNLM despeckling approach, the Frost despeckling approach, the Lee despeckling approach, the GNLDF despeckling approach, and the GSRBF despeckling approach, showed varying performance in removing speckle noise. The PNLM despeckling approach showed a relatively good performance in terms of alpha, CNR, or S-SNR, while its performance in terms of key assessing measures such as SNR, PSNR, beta, and FSIM is found to be poor. In addition, the images processed by the PNLM despeckling approach are usually accompanied by artifacts around cysts or at the sides of edges. The Frost despeckling approach and the Lee despeckling approaches showed better performance when applied to images corrupted by small speckle noise clusters or fine noise. The Frost despeckling approach, visually and numerically, has generally performed better than the Lee despeckling approach in suppressing speckle noise. The GNLDF despeckling approach showed better performance than the Frost despeckling approach or the Lee despeckling approach in suppressing speckle noise, yet images despeckled by the GNLDF despeckling approach suffered the spikes and the mistakenly preserved speckle noise clusters. The GSRBF despeckling approach is found efficient in suppressing speckle noise and results in good edge detection (beta), FSIM, and MSSIM. However, it shows a lagging performance in terms of CNR, S-SNR, SNR, PSNR when compared to the Lanczos despeckling approach of the present disclosure.

Although the SVD despeckling approach is used in the same procedure as the Lanczos despeckling approach, the two decomposition techniques differ in how effectively the orthonormal vectors contributing to signal are sorted. Sorting the orthonormal vectors based on the largest magnitudes of the summed columns of the tridiagonal matrix of the Lanczos despeckling approach is more accurate than sorting them merely on the largest magnitudes of the eigen values of the SVD despeckling approach. This has caused the SVD despeckling approach to be competitive in suppressing fine speckle noise and inefficient in suppressing rough speckle noise.

When one orthonormal vector is used per the 8×8 block size, the Lanczos and the SVD approaches would perform the same. However, when more orthonormal vectors are used, i.e., eight per the 8×8 block size or eight per the 16×16 block size, the Lanczos approach is more robust than SVD in suppressing speckle noise. This result differs when all orthonormal vectors are used, i.e., 64 per the 8×8 block size, where the orthogonal projection of the SVD and the Lanczos approaches performed the same (i.e., left the image undespeckled), while oblique projection has resulted in decorrelating and correlating the speckle noise samples through the SVD and the Lanczos approaches, respectively.

Overall, the Lanczos approach of the present disclosure demonstrated a robust despeckling approach based on the data shown above. It provides an attractive and a competitive computational complexity compared with the other approaches It has outperformed the SVD despeckling approach, the Frost despeckling approach, the Lee despeckling approach, the PNLM despeckling approach, the GNLDF despeckling approach, and the GSRBF despeckling approach in providing maximum suppression of speckle noise with a minimal sacrifice of image resolution and the least sacrifice of the original image structure.

The first embodiment is illustrated with respect to FIGS. 1-17. The first embodiment describes a method for suppressing speckle noise in medical ultrasound images. The method includes receiving, by a computing device having circuitry and program instructions configured to be executed by one or more processors, an n×m ultrasound envelope image matrix A formed by a plurality of pixels of the medical ultrasound image, segmenting, by the computing device, an n×m ultrasound envelope image matrix A into a number of overlapping segments of r×p size, to form a sub-matrix B for each overlapping segment, where n is an axial image index, m is a lateral image index, $0 \leq r \leq n$ and $0 \leq p \leq m$, reshaping each sub-matrix B into a column vector Z of size r·p×1, formulating a Hermitian covariance matrix C from the column vectors Z, forming a global covariance matrix G by averaging the Hermitian covariance matrices C by the number of overlapping segments of the image matrix A, applying Lanczos decomposition to the global covariance matrix G, generating an orthonormal vector matrix V composed of orthonormal vectors, v, generating a tridiagonal matrix H, summing each column of the tridiagonal matrix H to obtain a magnitude of each column, sorting the orthonormal vectors, v, of orthonormal vector matrix V in descending order based on the magnitude of each column, wherein sorting the orthonormal vectors divides the orthonormal vector matrix V into a signal subspace $V_1$ and a noise subspace $V_2$, forming an orthogonal projection matrix $P_{orth}$ from a first subset of the orthonormal vectors of signal subspace $V_1$, for each sub-matrix B, obtaining an estimated vector signal $\hat{Z}$ of size r·p×1 by projecting Z by $P_{orth}$, forming an estimated despeckled segment D of size r×p from the estimated vector signal $\hat{Z}$, reconstructing an estimated despeckled ultrasound image $\hat{I}$ by averaging each pixel of the plurality of pixels by the number of segment updates, and rendering, on a display of the computing device, the estimated despeckled ultrasound image $\hat{I}$.

The method further includes formulating the Hermitian covariance matrix C by transposing each column vector Z to form a transposition vector $Z^T$ and calculating the cross product of the column vector Z with its transposition vector $Z^T$, such that $C(t, s)=Z(t, s)\times Z^T(t, s)$, where $0 \leq t \leq n-r$ and $0 \leq s \leq m-p$.

The method further includes forming the global covariance matrix based on:

$$G = \frac{1}{(n-r+1)(m-p+1)} \sum_{\substack{0 \leq t \leq n-r \\ 0 \leq t \leq n-r}} C(t, s)$$

The orthonormal vector matrix is given by $V=[v_1\ v_2\ v_3\ \ldots\ v_{r\times p}]$.

The tridiagonal matrix H is given by:

$$H = \begin{bmatrix} \alpha_1 & \beta_1 & & & & \\ \beta_1 & \alpha_2 & \beta_2 & & & \\ & \beta_2 & \alpha_3 & & & \\ & & & \ddots & & \\ & & & & \alpha_{(x\times p)-1} & \beta_{(x\times p)-1} \\ & & & & \beta_{(x\times p)-1} & \alpha_{(x\times p)} \end{bmatrix}$$

where x=r and $\alpha$ and $\beta$ are obtained from the Lanczos decomposition.

The method further includes forming the signal subspace $V_1$, wherein $V_1=[v_1\ v_2\ v_3\ \ldots\ v_k]$, transposing the signal subspace $V_1$ to form a transposition vector $V_1^T$, and forming the orthogonal projection matrix based on $P_{orth}=V_1(V_1^T V_1)^{-1}V_1^T$.

The method further includes forming the noise subspace $V_2$ based on:

$V_2=[v_{k+1}\ v_{k+2}\ v_{k+3}\ \ldots\ v_{r\times p}]$.

The method further includes suppressing speckle noise in medical ultrasound images of a human kidney.

The method further includes suppressing speckle noise in medical ultrasound images of a human liver.

The second embodiment is illustrated with respect to FIGS. 1-17. The second embodiment describes a method for suppressing speckle noise in medical ultrasound images. The method includes receiving, by a computing device having circuitry and program instructions configured to be executed by one or more processors, an n×m ultrasound envelope image matrix A formed by a plurality of pixels of the medical ultrasound image, segmenting, by the computing device, an n×m ultrasound envelope image matrix A into a number of overlapping segments of r×p size, to form a sub-matrix B for each overlapping segment, where $0 \leq r \leq n$ and $0 \leq p \leq m$, reshaping each sub-matrix B into a column vector Z of size r·p×1, formulating a Hermitian covariance matrix C from the column vectors Z, forming a global covariance matrix G by averaging the Hermitian covariance matrices C by the number of overlapping segments of the image matrix A, applying Lanczos decomposition to the global covariance matrix G, generating an orthonormal vector matrix V composed of orthonormal vectors, v, generating a tridiagonal matrix H, summing each column of the tridiagonal matrix H to obtain a magnitude of each column, sorting the orthonormal vectors of orthonormal vector matrix V in descending order based on the magnitude of each column, wherein sorting the orthonormal vectors divides the orthonormal vector matrix V into a signal subspace $V_1$ and a noise subspace $V_2$, forming an orthogonal projection matrix $P_{orth}$ from a first subset of the orthonormal vectors of signal subspace $V_1$, forming an oblique projection matrix $P_{obli}$ from the orthonormal vectors V by subtracting each noise subspace $V_2$ from orthonormal vector matrix V, for each sub-matrix B, obtaining an estimated vector signal $\hat{Z}'$ of size r·p×1 by projecting Z by $P_{obli}$, forming an estimated despeckled segment D of size r×p from the estimated vector signal $\hat{Z}'$, reconstructing an estimated despeckled ultrasound image $\hat{I}$ by averaging each pixel of the plurality of pixels by the number of segment updates, and rendering, on a display of the computing device, the estimated despeckled ultrasound image $\hat{I}$.

The method further includes formulating the Hermitian covariance matrix C by transposing each column vector Z to form a transposition vector $Z^T$ and calculating the cross product of the column vector Z with its transposition vector $Z^T$, such that $C(t, s)=Z(t, s)\times Z^T(t, s)$, where $0 \leq t \leq n-r$ and $0 \leq s \leq m-p$.

The method further includes forming the global covariance matrix based on:

$$G = \frac{1}{(n-r+1)(m-p+1)} \sum_{\substack{0 \leq t \leq n-r \\ 0 \leq s \leq n-r}} C(t, s).$$

The orthonormal vector matrix is given by: $V=[v_1\ v_2\ v_3\ \ldots\ v_{r\times p}]$.

The tridiagonal matrix H is given by:

$$H = \begin{bmatrix} \alpha_1 & \beta_1 & & & \\ \beta_1 & \alpha_2 & \beta_2 & & \\ & \beta_2 & \alpha_3 & & \\ & & & \ddots & \\ & & & \alpha_{(x\times p)-1} & \beta_{(x\times p)-1} \\ & & & \beta_{(x\times p)-1} & \alpha_{(x\times p)} \end{bmatrix}$$

where x=r and α and β are obtained from the Lanczos decomposition.

The method further includes forming the signal subspace $V_1$, wherein $V_1=[v_1\ v_2\ v_3\ \ldots\ v_k]$, forming the signal subspace $V_2$, given by $V_2=[v_{k+1}\ v_{k+2}\ v_{k+3}\ \ldots\ v_{r\times p}]$, forming a null space S by subtracting each noise subspace $V_2$ from orthonormal vector matrix V, such that: $S=[v_{r\times p-k+1}\ v_{r\times p-k+2} v_{r\times p-k+3}\ \ldots\ v_{r\times p}]$, transposing the null space S to form a transposition vector $S^T$, and forming the oblique projection matrix based on: $P_{obli.}=P_{orth.}(1-(S^T P_w S)^{-1} S^T P_w)$.

The third embodiment is illustrated with respect to FIGS. 1-7. The third embodiment describes a non-transitory computer readable medium having instructions stored therein that, when executed by one or more processors, cause the one or more processors to perform a method for suppressing speckle noise in medical ultrasound images. The method includes receiving, by a computing device having circuitry and program instructions configured to be executed by one or more processors, an n×m ultrasound envelope image matrix A formed by a plurality of pixels of the medical ultrasound image, segmenting, by the computing device, an n×m ultrasound envelope image matrix A into a number of overlapping segments of r×p size, to form a sub-matrix B for each overlapping segment, where n is an axial image index, m is a lateral image index, $0 \leq r \leq n$ and $0 \leq p \leq m$, reshaping each sub-matrix B into a column vector Z of size r·p×1, formulating a Hermitian covariance matrix C from the column vectors Z, forming a global covariance matrix G by averaging the Hermitian covariance matrices C by the number of overlapping segments of the image matrix A, applying Lanczos decomposition to the global covariance matrix G, generating an orthonormal vector matrix V composed of orthonormal vectors, v, generating a tridiagonal matrix H, summing each column of the tridiagonal matrix H to obtain a magnitude of each column, sorting the orthonormal vectors, v, of orthonormal vector matrix V in descending order based on the magnitude of each column, wherein sorting the orthonormal vectors divides the orthonormal vector matrix V into a signal subspace $V_1$ and a noise subspace $V_2$, and forming an orthogonal projection matrix $P_{orth}$ from a first subset of the orthonormal vectors of signal subspace $V_1$.

The method further includes for each sub-matrix B, obtaining an estimated vector signal $\hat{Z}$ of size r·p×1 by projecting Z by $P_{orth}$, forming an estimated despeckled segment D of size r×p from the estimated vector signal $\hat{Z}$, reconstructing an estimated despeckled ultrasound image $\hat{I}$ by averaging each pixel of the plurality of pixels by the number of segment updates, and rendering, on a display of the computing device, the estimated despeckled ultrasound image $\hat{I}$.

The method further includes forming the signal subspace $V_1$, wherein $V_1=[v_1\ v_2\ v_3\ \ldots\ v_k]$, transposing the signal subspace $V_1$ to form a transposition vector $V_1^T$, and forming the orthogonal projection matrix based on $P_{orth}=V_1 (V_1^T V_1)^{-1} V_1^T$.

The method further includes forming an oblique projection matrix $P_{obli}$ from the orthonormal vectors V by subtracting each noise subspace $V_2$ from orthonormal vector matrix V, for each sub-matrix B, obtaining an estimated vector signal $\hat{Z}'$ of size r·p×1 by projecting Z by $P_{obli}$, forming an estimated despeckled segment D of size r×p from the estimated vector signal $\hat{Z}'$, reconstructing an estimated despeckled ultrasound image $\hat{I}$ by averaging each pixel of the plurality of pixels by the number of segment updates and rendering, on a display of the computing device, the estimated despeckled ultrasound image $\hat{I}$.

The method further includes forming the signal subspace $V_1$, wherein $V_1=[v_1\ v_2\ v_3\ \ldots\ v_k]$, forming the signal subspace $V_2$, given by $V_2=[v_{k+1}\ v_{k+2}\ v_{k+3}\ \ldots\ v_{r\times p}]$, forming a null space S by subtracting each noise subspace $V_2$ from orthonormal vector matrix V, such that: $S=[v_{r\times p-k+1}\ v_{r\times p-k+2} v_{r\times p-k+3}\ \ldots\ v_{r\times p}]$, transposing the null space S to form a transposition vector $S^T$, and forming the oblique projection matrix based on: $P_{obli.}=P_{orth.}(1-(S^T P_w S)^{-1} S^T P_w)$.

Figure 13:
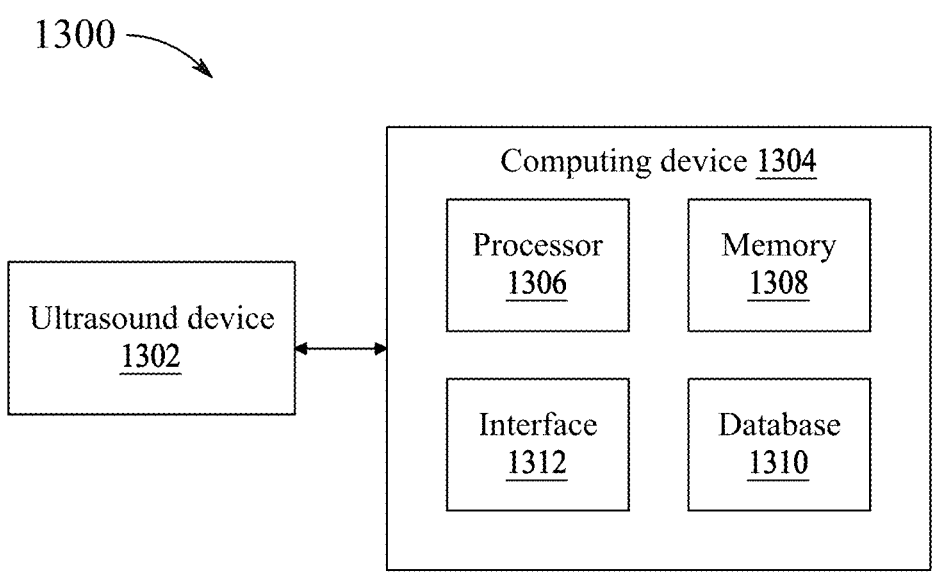
FIG. 13 illustrates a system for processing ultrasound images, according to aspects of the present disclosure.

FIG. 13 illustrates a system 1300 for processing ultrasound images. The system 1300 includes an ultrasound imaging system 1302 (also referred to ultrasound device), and a computing device 1304. The system 1300 includes the computing device 1304 that performs suppression of speckle noise in the ultrasound images. The computing device 1304 may be a part of the ultrasound device 1302 or may be the ultrasound device 1302 itself. The computing device 1204 includes, inter alia, a processor 1306, a memory 1308, a database 1310, and an interface 1312 to support the image processing operation including suppressing speckle noise in the medical ultrasound images.

The computing device 1304 is a special purpose device designed for performing performs suppression of speckle noise in the ultrasound images. The computing device 1304 includes a communication device (not shown) for receiving and communicating data with other devices. For example, the communication device receives measurements such as n measurements from ultrasound device 1302 from the external devices through interface 1312. The memory 1308 includes instructions stored therein that, when executed by one or more processors, cause the one or more processors to perform a method for suppressing speckle noise in medical ultrasound images. The database 1310 may store machine instructions to process ultrasound images to suppress speckle noise, medical ultrasound images, processed images, comparison reports, and such information. The computing device 1304 may also include an I/O, a keyboard, a printer, a display, and a communication bus(not shown). The computing device 1304 may include program instructions which may be executed by the processor (s) 1306. Next, further details of the hardware description of the computing environment of FIG. 13 according to exemplary embodiments is described with reference to FIG. 14.

Figure 14:
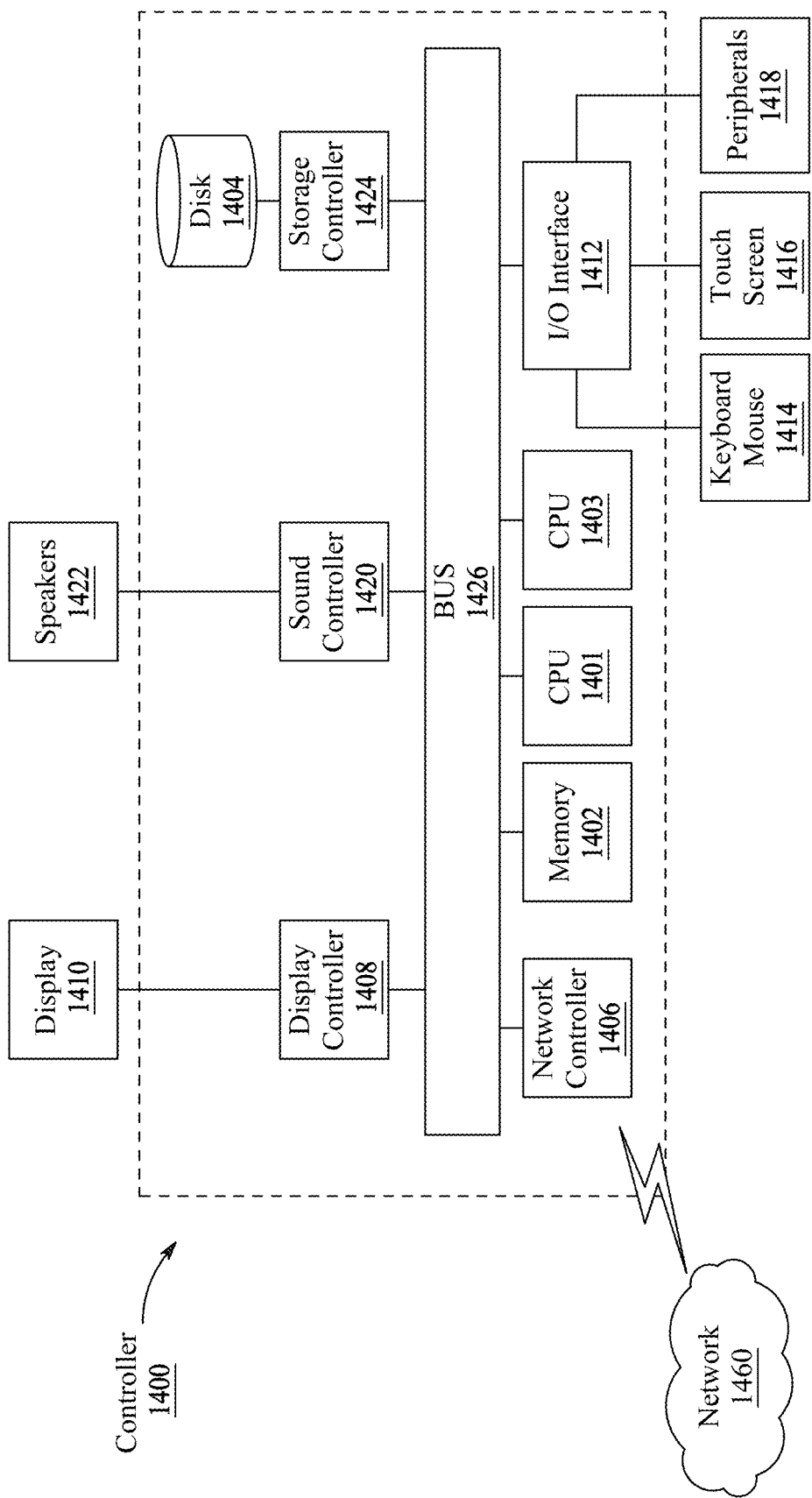
FIG. 14 is an illustration of a non-limiting example of details of computing hardware used in the computing device, according to certain embodiments.

In FIG. 14, a controller 1400 is described as representative of the computing device 1300 of FIG. 13, which includes a CPU 1401 which performs the processes described above/below. The process data and instructions may be stored in memory 1402. These processes and instructions may also be stored on a storage medium disk 1404 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 1401, 1403 and an operating system such as Microsoft Windows 7, Microsoft Windows 10, UNIX, Solaris, LINUX, Apple MAC-OS and other systems known to those skilled in the art.

The hardware elements in order to achieve the computing device may be realized by various circuitry elements, known to those skilled in the art. For example, CPU 1401 or CPU 1403 may be a Xenon or Core processor from Intel of America or an Opteron processor from AMD of America, or may be other processor types that would be recognized by one of ordinary skill in the art. Alternatively, the CPU 1401, 1403 may be implemented on an FPGA, ASIC, PLD or using discrete logic circuits, as one of ordinary skill in the art would recognize. Further, CPU 1401, 1403 may be implemented as multiple processors cooperatively working in parallel to perform the instructions of the inventive processes described above.

The computing device in FIG. 14 also includes a network controller 1406, such as an Intel Ethernet PRO network interface card from Intel Corporation of America, for interfacing with network 1460. As can be appreciated, the network 1460 can be a public network, such as the Internet, or a private network such as an LAN or WAN network, or any combination thereof and can also include PSTN or ISDN sub-networks. The network 1460 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 1408, such as a NVIDIA GeForce GTX or Quadro graphics adaptor from NVIDIA Corporation of America for interfacing with display 1410, such as a Hewlett Packard HPL2445w LCD monitor. A general purpose I/O interface 1412 interfaces with a keyboard and/or mouse 1414 as well as a touch screen panel 1416 on or separate from display 1410. General purpose I/O interface also connects to a variety of peripherals 1418 including printers and scanners, such as an OfficeJet or DeskJet from Hewlett Packard.

A sound controller 1420 is also provided in the computing device such as Sound Blaster X-Fi Titanium from Creative, to interface with speakers/microphone 1422 thereby providing sounds and/or music.

The general purpose storage controller 1424 connects the storage medium disk 1404 with communication bus 1426, which may be an ISA, EISA, VESA, PCI, or similar, for interconnecting all of the components of the computing device. A description of the general features and functionality of the display 1410, keyboard and/or mouse 1414, as well as the display controller 1408, storage controller 1424, network controller 1406, sound controller 1420, and general purpose I/O interface 1412 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 15.

Figure 15:
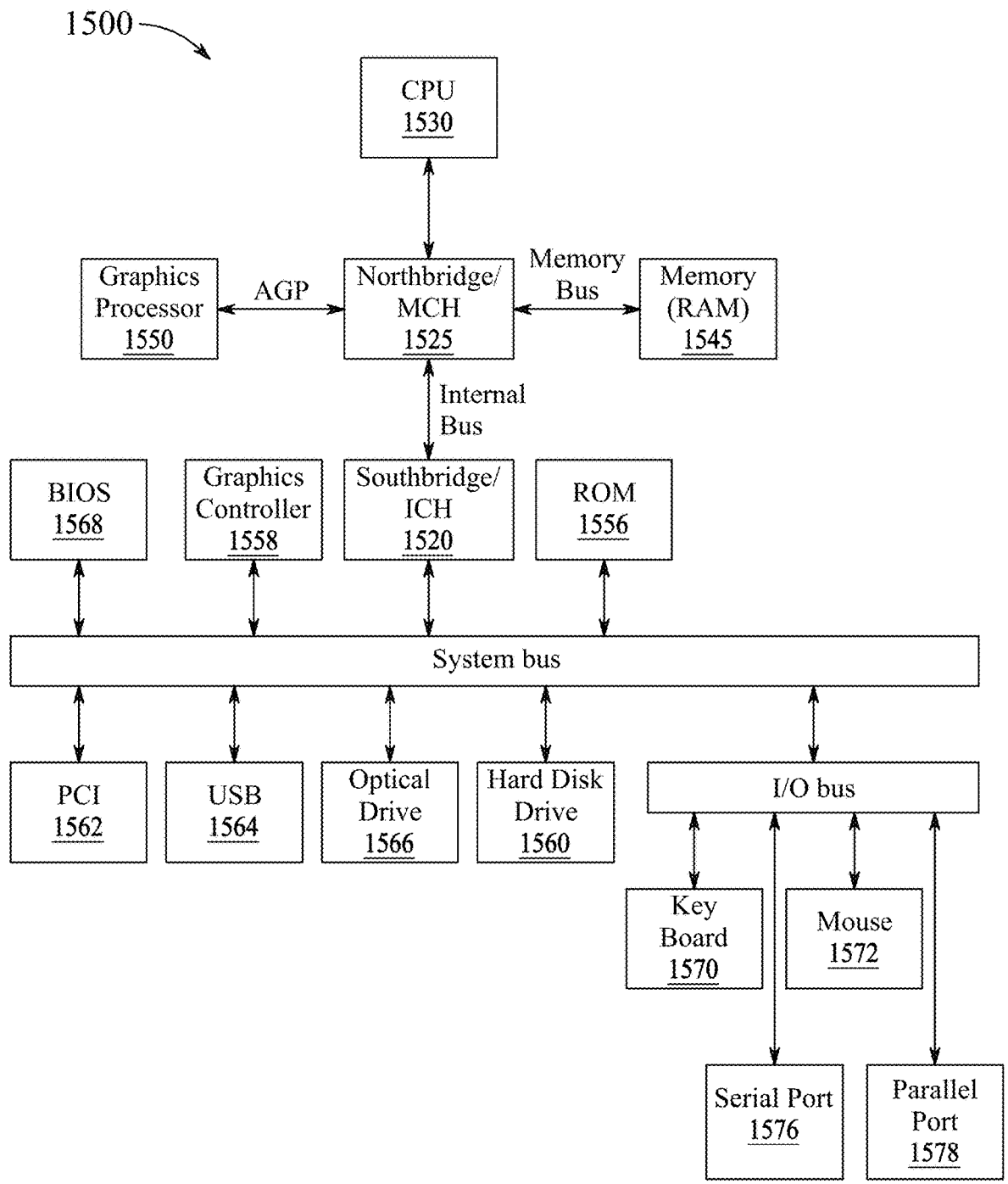
FIG. 15 is an exemplary schematic diagram of a data processing system used within the computing device, according to certain embodiments.

FIG. 15 shows a schematic diagram of a data processing system, according to certain embodiments, for performing the functions of the exemplary embodiments. The data processing system is an example of a computer in which code or instructions implementing the processes of the illustrative embodiments may be located.

In FIG. 15, data processing system 1500 employs a hub architecture including a north bridge and memory controller hub (NB/MCH) 1525 and a south bridge and input/output (I/O) controller hub (SB/ICH) 1520. The central processing unit (CPU) 1530 is connected to NB/MCH 1525. The NB/MCH 1525 also connects to the memory 1545 via a memory bus, and connects to the graphics processor 1550 via an accelerated graphics port (AGP). The NB/MCH 1525 also connects to the SB/ICH 1520 via an internal bus (e.g., a unified media interface or a direct media interface). The CPU Processing unit 1530 may contain one or more processors and even may be implemented using one or more heterogeneous processor systems.

Figure 16:
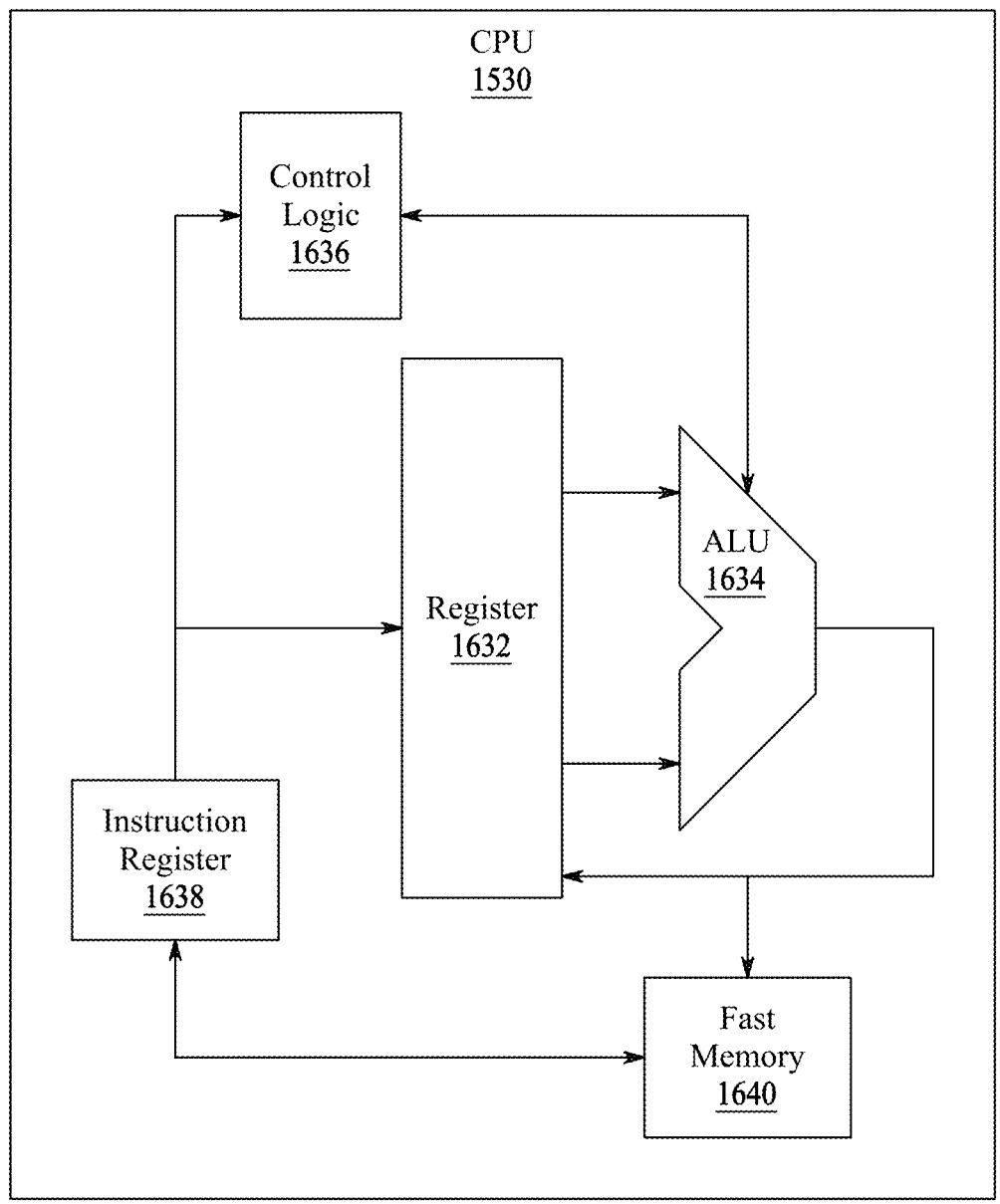
FIG. 16 is an exemplary schematic diagram of a processor used with the computing device, according to certain embodiments.

For example, FIG. 16 shows one implementation of CPU 1530. In one implementation, the instruction register 1638 retrieves instructions from the fast memory 1640. At least part of these instructions are fetched from the instruction register 1638 by the control logic 1636 and interpreted according to the instruction set architecture of the CPU 1530. Part of the instructions can also be directed to the register 1632. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 1634 that loads values from the register 1632 and performs logical and mathematical operations on the loaded values according to the instructions. The results from these operations can be feedback into the register and/or stored in the fast memory 1640. According to certain implementations, the instruction set architecture of the CPU 1530 can use a reduced instruction set architecture, a complex instruction set architecture, a vector processor architecture, a very large instruction word architecture. Furthermore, the CPU 1530 can be based on the Von Neuman model or the Harvard model. The CPU 1530 can be a digital signal processor, an FPGA, an ASIC, a PLA, a PLD, or a CPLD. Further, the CPU 1530 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 15, the data processing system 1500 can include that the SB/ICH 1520 is coupled through a system bus to an I/O Bus, a read only memory (ROM) 1556, universal serial bus (USB) port 1564, a flash binary input/output system (BIOS) 1568, and a graphics controller 1558. PCI/PCIe devices can also be coupled to SB/ICH 1588 through a PCI bus 1562.

The PCI devices may include, for example, Ethernet adapters, add-in cards, and PC cards for notebook computers. The Hard disk drive 1560 and CD-ROM 1566 can use, for example, an integrated drive electronics (IDE) or serial advanced technology attachment (SATA) interface. In one implementation the I/O bus can include a super I/O (SIO) device.

Further, the hard disk drive (HDD) 1560 and optical drive 1566 can also be coupled to the SB/ICH 1520 through a system bus. In one implementation, a keyboard 1570, a mouse 1572, a parallel port 1578, and a serial port 1576 can be connected to the system bus through the I/O bus. Other peripherals and devices that can be connected to the SB/ICH 1520 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 17:
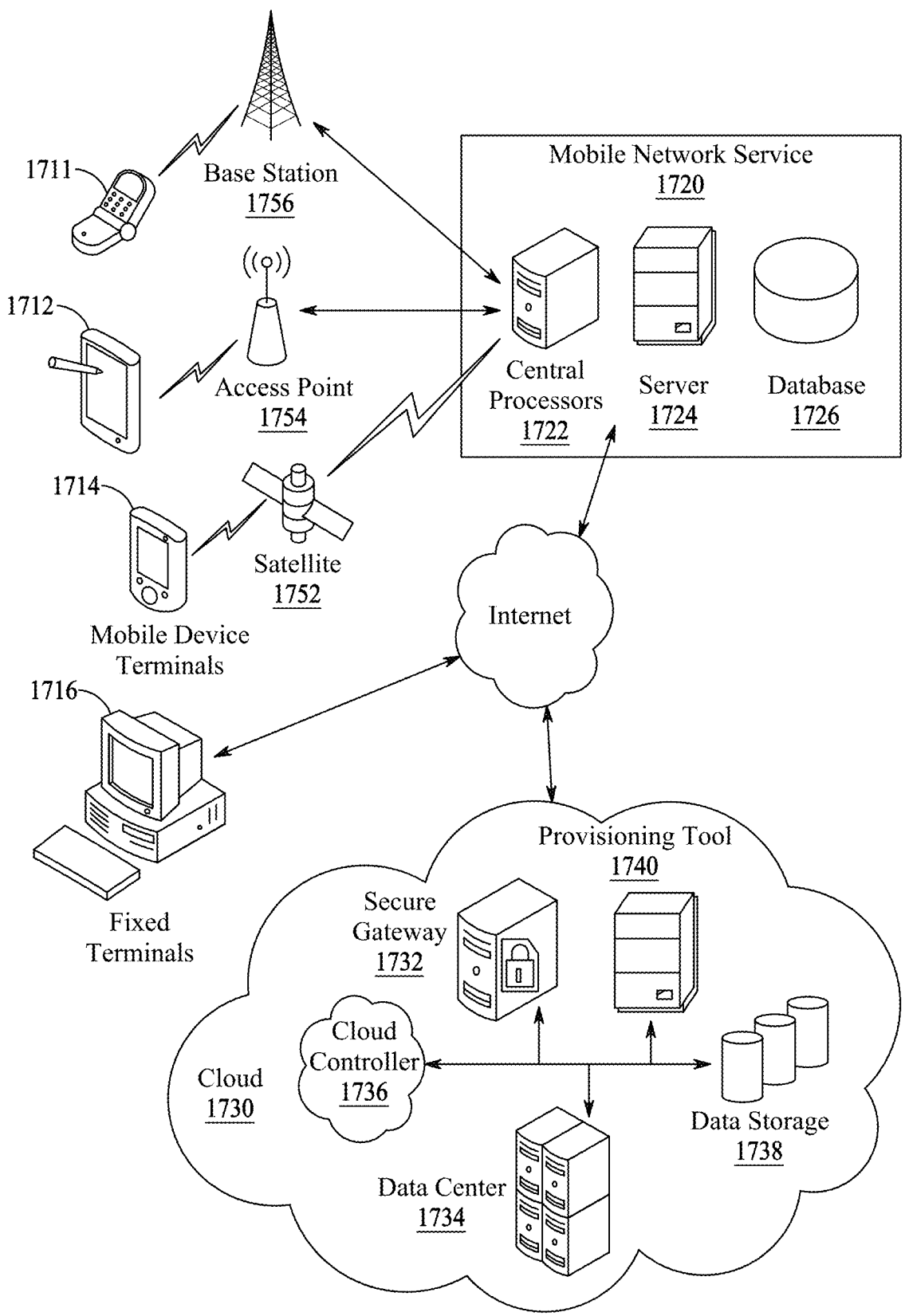
FIG. 17 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 17, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method for suppressing speckle noise in medical ultrasound images, comprising:
    receiving, by a computing device having circuitry and program instructions configured to be executed by one or more processors, an n×m ultrasound envelope image matrix A formed by a plurality of pixels of the medical ultrasound image;
    segmenting, by the computing device, the n×m ultrasound envelope image matrix A into a number of overlapping segments of r×p size;
    forming a sub-matrix B for each overlapping segment, where n is an axial image index, m is a lateral image index, and where 0≤r≤n and 0≤p≤m;
    reshaping each sub-matrix B into a column vector Z of size r·p×1;
    formulating a Hermitian covariance matrix C from the column vectors Z for each overlapping segment;
    forming a global covariance matrix G of size r·p×r·p by summing the formulated Hermitian covariance matrices C and dividing the sum by the number of overlapping segments of r×p size of the image matrix A;
    applying Lanczos decomposition to the global covariance matrix G to generate an orthonormal vector matrix V composed of orthonormal vectors $v_n$, where n=1, 2, . . . , $v_{r \times p}$ and a symmetric tridiagonal matrix H, wherein H has diagonal elements defined by $h_{nn}$ for n=1, . . . n, and subdiagonal elements and superdiagonal elements defined by $h_{n+1,n}$, where $h_{nn}=v_n$ transposed, times the n×m ultrasound envelope image matrix A, times $v_n$;
    summing each column of the tridiagonal matrix H to obtain a magnitude of each column;
    sorting the orthonormal vectors $v_n$ of the orthonormal vector matrix V in descending order based on the magnitude of each column, wherein sorting the orthonormal vectors divides the orthonormal vector matrix V into a signal subspace $V_1$ and a noise subspace $V_2$;
    forming an orthogonal projection matrix $P_{orth}$ from a first subset of the orthonormal vectors of the signal subspace $V_1$;
    for each sub-matrix B, obtaining an estimated vector signal $\hat{Z}$ of size r·p×1 by projecting the column vectors Z by $P_{orth}$;
    forming an estimated despeckled segment D of size r×p from the estimated vector signal $\hat{Z}$;
    updating each of the overlapping segments of size r×p of the n×m ultrasound envelope image matrix A with the estimated despeckled segment D of size r×p;
    reconstructing an estimated despeckled ultrasound image $\hat{I}$ by averaging each pixel of the plurality of pixels by the number of updated overlapping segments; and
    rendering, on a display of the computing device, the estimated despeckled ultrasound image $\hat{I}$.

2. The method of claim 1, further comprising:
    formulating the Hermitian covariance matrix C by transposing each column vector Z to form a transposition vector $Z^T$ and calculating the cross product of the column vector Z with its transposition vector $Z^T$ such that $C(t, s)=Z(t, s) \times Z^T(t, s)$, where $0 \le t \le n-r$ and $0 \le s \le m-p$, where t and s are pixel shifts between each Hermitian covariance matrix C and r and p are the size of the overlapping segments of the ultrasound envelope image matrix A.

3. The method of claim 1, further comprising:

forming the signal subspace $V_1$ such that $V_1=[v_1 \; v_2 \; v_3 \ldots v_k]$, where v1, v2, ... vk are the orthonormal vectors and $k<(r \times p)$;

transposing the signal subspace $V_1$ to form a transposition vector $V_1^T$; and forming the orthogonal projection matrix $P_{orth}$ based on $P_{orth}=V_1(V_1^T V_1)^{-1} V_1^T$.

4. The method of claim 3, further comprising:

forming the noise subspace $V_2$ based on $V_2=[v_{k+1} \; v_{k+2} \; v_{k+3} \ldots v_{r \times p}]$.

5. The method of claim 1, wherein the medical ultrasound images include a human kidney.

6. The method of claim 1, wherein the medical ultrasound images include a human liver.

7. A method for suppressing speckle noise in medical ultrasound images, comprising:

receiving, by a computing device having circuitry and program instructions configured to be executed by one or more processors, an n×m ultrasound envelope image matrix A formed by a plurality of pixels of the medical ultrasound image;

segmenting, by the computing device, the n×m ultrasound envelope image matrix A into a number of overlapping segments of r×p size;

forming a sub-matrix B for each overlapping segment, where n is an axial image index, m is a lateral image index, and where $0 \le r \le n$ and $0 \le p \le m$;

reshaping each sub-matrix B into a column vector Z of size r·p×1;

formulating a Hermitian covariance matrix C from the column vectors Z for each overlapping segment;

forming a global covariance matrix G of size r·p×r·p by summing each of the formulated Hermitian covariance matrices C and dividing the sum by the number of overlapping segments of r×p size of the image matrix A;

applying Lanczos decomposition to the global covariance matrix G to generate an orthonormal vector matrix V composed of orthonormal vectors $v_n$, where n=1, 2, ..., $v_{r \times p}$ and a symmetric tridiagonal matrix H having diagonal elements defined by $h_{nn}$ for n=1, ... n, and subdiagonal elements and superdiagonal elements defined by $h_{n+1,n}$, where $h_{nn}=v_n$ transposed times the n×m ultrasound envelope image matrix A times $v_n$;

summing each column of the tridiagonal matrix H to obtain a magnitude of each column;

sorting the orthonormal vectors $v_n$ of the orthonormal vector matrix V in descending order based on the magnitude of each column, wherein sorting the orthonormal vectors $v_n$ divides the orthonormal vector matrix V into a signal subspace $V_1$ and a noise subspace $V_2$;

forming an orthogonal projection matrix $P_{orth}$ from a first subset of the orthonormal vectors $v_n$ of the signal subspace $V_1$;

forming an oblique projection matrix $P_{obli}$ by subtracting each noise subspace $V_2$ from the orthonormal vector matrix V;

for each sub-matrix B, obtaining an estimated vector signal $\hat{Z}'$ of size r·p×1 by projecting the column vectors Z by $P_{obli}$;

forming an estimated despeckled segment D of size r×p from the estimated vector signal $\hat{Z}'$;

updating each of the overlapping segments of size r×p of the n×m ultrasound envelope image matrix A with the estimated despeckled segment D of size r×p;

reconstructing an estimated despeckled ultrasound image $\hat{I}$ by averaging each pixel of the plurality of pixels by the number of segment updates; and rendering, on a display of the computing device, the estimated despeckled ultrasound image $\hat{I}$.

8. The method of claim 7, further comprising:

formulating the Hermitian covariance matrix C by transposing each column vector Z to form a transposition vector $Z^T$ and calculating the cross product of the column vector Z with its transposition vector $Z^T$, such that $C(t, s)=Z(t, s) \times Z^T(t, s)$, where $0 \le t \le n-r$ and $0 \le s \le m-p$, where t and s are pixel shifts between each Hermitian covariance matrix C and r and p are the size of the overlapping segments of the ultrasound envelope image matrix A.

9. The method of claim 7, further comprising:

forming the signal subspace $V_1$ such that $V_1=[v_1 \; v_2 \; v_3 \ldots v_k]$, where v1, v2, ... vk are the orthonormal vectors and $k<(r \times p)$;

forming the noise subspace $V_2$, given by $V_2=[v_{k+1} \; v_{k+2} \; v_{k+3} \ldots v_{r \times p}]$;

forming a null space S by subtracting each noise subspace $V_2$ from orthonormal vector matrix V, such that:

$S=[V_{r \times p-k+1} V_{r \times p-k+2} V_{r \times p-k+3} \ldots V_{r \times p}]$;

transposing the null space S to form a transposition vector $S^T$; and forming the oblique projection matrix based on: $P_{obli.}=P_{orth.}(1-S(S^T P_w S)^{-1} S^T P_w)$, where W is a null space of the orthogonal projection matrix $P_{orth}$ given by $P_w=I-P_{orth}$, where I is an identity matrix.

10. The method of claim 1, wherein the medical ultrasound images include a human lymph node.

11. The method of claim 1, further comprising:

generating, with an ultrasonic transducer with 64 active elements, ultrasonic waves at a center frequency of 3.5 MHz;

sampling, by 256 radio frequency lines, samples each having 256 ultrasonic echoes at a sampling frequency of 100 MHz;

envelope detecting, by a Hilbert transform, each of the 256 ultrasonic echoes;

decimating the envelope by a factor of 16; and generating the n×m ultrasound envelope image matrix A, where n=m=256.

* * * * *